(12) United States Patent
Hori et al.

(10) Patent No.: US 6,331,521 B1
(45) Date of Patent: Dec. 18, 2001

(54) ECHINOCANDINE DERIVATIVES WITH ANTIMICROBIAL ACTIVITY

(75) Inventors: Yasuhiro Hori, Tsukuba-gun; Yasuhisa Tsurumi, Tsukuba; Shigehiro Takase, Ishioka; Hiroshi Hatanaka, Kitasouma-gun; Kazutoshi Sakamoto, Tsuchiura; Seiji Hashimoto, Tsukuba; Hidenori Ohki, Takarazuka; Takashi Tojo, Osaka; Keiji Matsuda, Takatsuki; Kohji Kawabata, Kawanishi, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/423,654

(22) PCT Filed: May 18, 1998

(86) PCT No.: PCT/JP98/02168

§ 371 Date: Dec. 1, 1999

§ 102(e) Date: Dec. 1, 1999

(87) PCT Pub. No.: WO98/52967

PCT Pub. Date: Nov. 26, 1998

(30) Foreign Application Priority Data

May 21, 1997 (AU) .................................. PO6918

(51) Int. Cl.[7] .............................. A61K 38/00; C07K 5/00; C07K 7/00; C07K 7/56
(52) U.S. Cl. .................................. 514/9; 514/11; 530/300; 530/317; 530/33
(58) Field of Search .................... 514/9, 11; 530/333, 530/317

(56) References Cited

FOREIGN PATENT DOCUMENTS

| 0431350 | * | 6/1991 | (EP) | ................. | C07K/7/56 |
| 2246134 | * | 1/1992 | (GB) | ................. | C07K/7/56 |
| 9852967 | * | 11/1998 | (WO) | ................. | C07K/7/56 |

OTHER PUBLICATIONS

Iwamoto et al., *J. of Antibiotics*, vol. 47 No. 10, Oct. 1994, pp. 1084–1091.*

* cited by examiner

*Primary Examiner*—Avis M. Davenport
(74) *Attorney, Agent, or Firm*—Oblon, Spivak, McClelland, Maier & Neustadt, P.C.

(57) ABSTRACT

The invention relates to new polypeptide compounds represented by the following formula [I]:

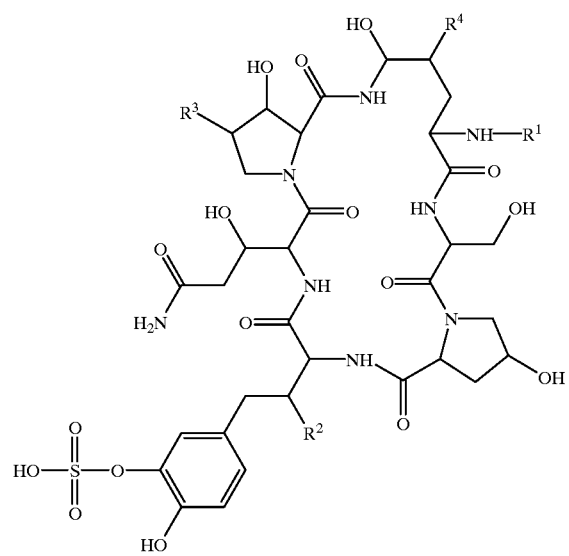

wherein $R^1$ is hydrogen, etc, $R^2$ is hydrogen, etc, $R^3$ is hydrogen, etc, and $R^4$ is hydrogen, etc, or a salt thereof which have antimicrobial activities (especially, antifungal activities), inhibitory activity on β-1, 3-glucan synthase, to process for preparation thereof, to a pharmaceutical composition comprising the same, and to a method for the prophylactic and/or therapeutic treatment of infectious diseases including *Pneumocystis carinii* infection (e.g. *Pneumocystis carinii* pneumonia) in a human being or an animal.

15 Claims, No Drawings

ECHINOCANDINE DERIVATIVES WITH ANTIMICROBIAL ACTIVITY

TECHNICAL FIELD

The present invention relates to new polypeptide compounds and salts thereof which are useful as a medicament.

BACKGROUND ART

In U.S. Pat. Nos. 5,376,634, 5,502,033, etc., there are disclosed the polypeptide compound and a salt thereof, which have antimicrobial activities (especially antifungal activity).

DISCLOSURE OF INVENTION

The present invention relates to new polypeptide compounds (hereinafter referred to as WF 738 derivative) and salts thereof.

More particularly, it relates to new polypeptide compound and salts thereof, which have antimicrobial activities [especially, antifungal activities, in which the fungi may include Asperaillus, Cryptococcus, Candida, Mucor, Actinomyces, Histoplasma, Dermatophyte, Malassezia, Fusarium and the like.], inhibitory activity on β-1,3-glucan synthase, and further which are expected to be useful for the prophylactic and/or therapeutic treatment of *Pneumocystis carinii* infection (e.g. *Pneumocystis carinii* pneumonia) in a human being or an animal, to a process for preparation thereof, to a pharmaceutical composition comprising the same, and to a method for the prophylactic and/or therapeutic treatment of infectious diseases including *Pneumocystis carinii* infection (e.g. *Pneumocystis carinii* pneumonia) in a human being or an animal.

The object polypeptide compound of the present invention is new and can be represented by the following general formula [I]:

[I]

wherein
$R^1$ is hydrogen or acyl group,
$R^2$ is hydrogen or hydroxy,
$R^3$ is hydrogen or methyl, and
$R^4$ is hydrogen or hydroxy, with proviso that when $R^4$ is hydroxy, then $R^2$ is hydroxy, or a salt thereof.

The polypeptide compound [I] of the present invention can be prepared by the processes as illustrated in the following schemes.

Process 1 a strain belonging to the Coleophoma which is capable of producing the compound [Ia] or a salt thereof —fermentation→

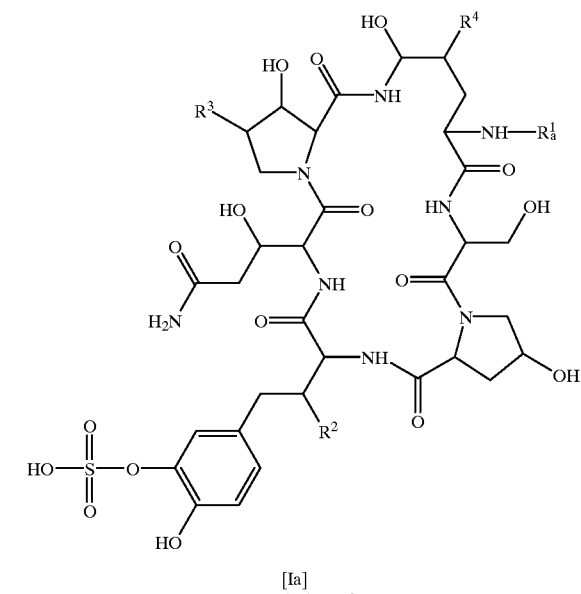

[Ia]
or a salt thereof

Process 2

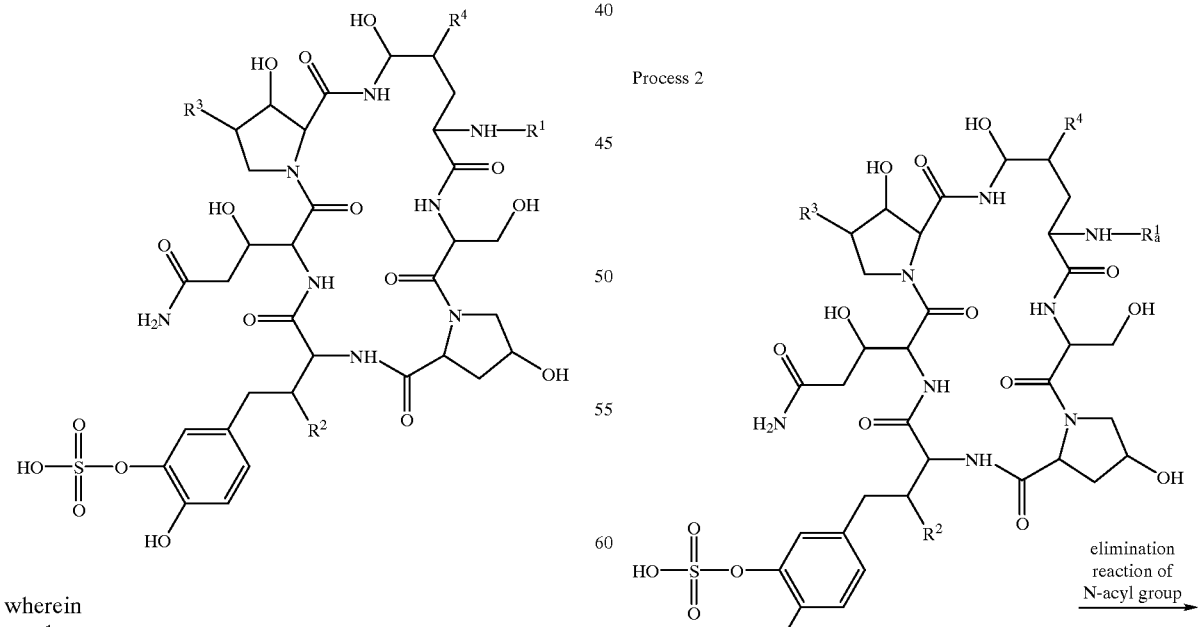

[Ia]
or a salt thereof

—elimination reaction of N-acyl group→

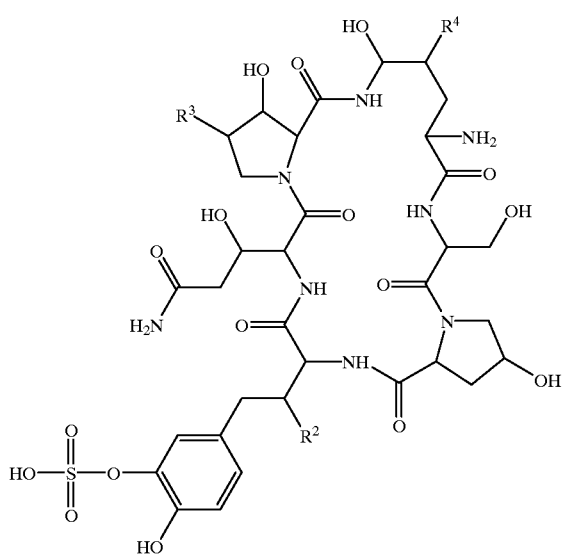

[Ib] or a salt thereof

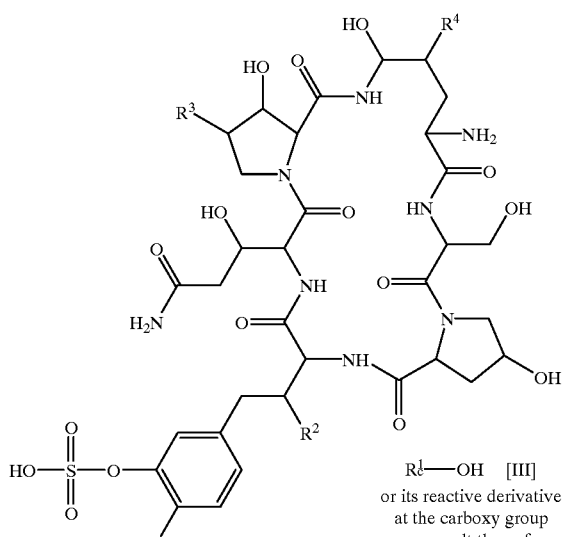

[Ic] or a salt thereof wherein
R$_a^1$ is higher alkanoyl, and
R$_c^1$ is acyl group exclusive of palmitoyl,
R$^2$, R$^3$ and R$^4$ are each as defined above.

Suitable salt of the object compound [I] is pharmaceutically acceptable and conventional non-toxic mono or di salt and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, N,N-diisopropylethylamine salt, pyridine salt, picoline salt, dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.], and the like.

In the above and subsequent descriptions of the present specification, suitable examples and illustration of the various definitions which the present invention intends to include within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated.

The term "one or more" may be the number of 1 to 6, unless otherwise indicated.

Suitable example of "halogen" may be fluoro, chloro, bromo, iodo, and the like.

Suitable example of "lower alkoxy" may include straight or branched one such as methoxy, ethoxy, propoxy, isopropoxy, butoxy, isobutoxy, tert-butoxy, pentyloxy, tert-pentyloxy, neo-pentyloxy, hexyloxy, isohexyloxy, and the like, in which the preferred one may be propoxy, pentyloxy and hexyloxy.

Suitable example of "higher alkoxy" may include straight or branched one such as heptyloxy, octyloxy, 3,5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy, icosyloxy, and the like, in which the preferred one may be ($C_7$–$C_{14}$)alkoxy, and the most preferred one may be octyloxy.

Suitable example of "lower alkyl" may include straight or branched one having 1 to 6 carbon atom(s), such as methyl, ethyl, propyl, isopropyl, butyl, isobutyl, sec-butyl, tert-butyl, pentyl, tert-pentyl, neo-pentyl, hexyl, isohexyl, and the like.

Suitable example of "higher alkyl" may include straight or branched one having 7 to 20 carbon atoms, such as heptyl, octyl, 3,5-dimethyloctyl, 3,7-dimethyloctyl, nonyl, decyl, undecyl, dodecyl, tridecyl, tetradecyl, pentadecyl, hexadecyl, heptadecyl, octadecyl, nonadecyl, icosyl, and the like.

Suitable example of "aryl" and "ar" moiety may include phenyl which may have lower alkyl (e.g., phenyl, mesityl, tolyl, etc.), naphthyl, anthryl, and the like, in which the preferred one may be phenyl.

Suitable example of "aroyl" may include benzoyl, toluoyl, naphthoyl, anthrylcarbonyl, and the like, in which the preferred one may be benzoyl.

Suitable example of "heterocyclic group" and "heterocyclic" moiety may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s) for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 or 6-membered) heteromonocyclic group containing an oxygen atom, for example, furyl, etc.;

saturated 3 to 8-membered (more preferably 5 or 6-membered) heteromonocyclic group containing an oxygen atom, for example, tetrahydrofuran, tetrahydropyran, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

Suitable example of "acyl group" may include aliphatic acyl, aromatic acyl, heterocyclic acyl, arylaliphatic acyl and heterocyclic-aliphatic acyl derived from carboxylic acid, carbonic acid, carbamic acid, sulfonic acid, and the like.

Suitable example of the "acyl group" thus explained may be:

lower alkanoyl [e.g. formyl, acetyl, propionyl, butyryl, isobutyryl, valeryl, hexanoyl, pivaloyl, etc.] which may have one or more (preferably 1 to 3) suitable substituent(s) such as halogen, aryl which may have one or more (preferably 1 to 3) suitable substituent(s) such as hydroxy; higher alkoxy; aryl; or the like, lower alkoxy, amino, protected amino, (preferably, acylamino) such as lower alkoxycarbonylamino (e.g. methoxycarbonylamino, ethoxycarbonylamino, propoxycarbonylamino, butoxycarbonylamino, t-butoxycarbonylamino, pentyloxycarbonylamino, hexyloxycarbonylamino, etc.); ar(lower)alkoxycarbonylamino such as phenyl(lower)alkoxycarbonylamino (e.g. benzyloxycarbonylamino, etc.); or the like, di(lower)alkylamino (e.g. dimethylamino, N-methylethylamino, diethylamino, N-propylbutylamino, dipentylamino, dihexylamino, etc.), lower alkoxyimino (e.g. methoxyimino, ethoxyimino, propoxyimino, butoxyimino, t-butoxyimino, pentyloxyimino, hexyloxyimino, etc.), ar(lower)alkoxyimino such as phenyl(lower)alkoxyimino (e.g. benzyloxyimino, phenethyloxyimino, benzhydryloxyimino, etc.) which may have one or more (preferably 1 to 3) suitable substituent(s) like higher alkoxy, or the like, heterocyclicthio (preferably, pyridylthio) which may have one or more (preferably 1 to 3) suitable substituent (s) like higher alkyl, heterocyclic group which may have one or more (preferably 1 to 3) suitable substituent(s) such as amino; aforesaid protected amino; higher alkyl; or the like, or the like, higher alkanoyl [e.g. heptanoyl, octanoyl, nonanoyl, decanoyl, undecanoyl, lauroyl, tridecanoyl, myristoryl, pentadecanoyl, palmitoyl, 10,12-dimethyltetradecanoyl, heptadecanoyl, stearoyl, nonadecanoyl, icosanoyl, etc.], in which the preferred one may be ($C_7$–$C_{17}$)alkanoyl, and the most preferred one may be palmitoyl, lower alkenoyl [e.g. acryloyl, methacryloyl, crotonoyl, 3-pentenoyl, 5-hexenoyl, etc.] which may have one or more (preferably 1 to 3) suitable substituent(s) such as aryl which may have one or more (preferably 1 to 3) suitable substituent (s) like higher alkoxy, or the like, higher alkenoyl [e.g. 4-heptenoyl, 3-octenoyl, 3,6-decadienoyl, 3,7,11-trimethyl-2,6,10-dodecatrienoyl, 4,10-heptadecadienoyl, etc.], lower alkoxycarbonyl [e.g. methoxycarbonyl, ethoxycarbonyl, propoxycarbonyl, butoxycarbonyl, t-butoxycarbonyl, pentyloxycarbonyl, hexyloxycarbonyl, etc.], higher alkoxycarbonyl [e.g. heptyloxycarbonyl, octyloxycarbonyl, 2-ethylhexyloxycarbonyl, nonyloxycarbonyl, decyloxycarbonyl, 3,7-dimethyloctyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexadecyloxycarbonyl, heptadecyloxycarbonyl, octadecyloxycarbonyl, nonadecyloxycarbonyl, icosyloxycarbonyl, etc.], aryloxycarbonyl [e.g. phenoxycarbonyl, naphthyloxycarbonyl, etc.], arylglyoxyloyl [e.g. phenylglyoxyloyl, naphthylglyoxyloyl, etc.], ar(lower)alkoxycarbonyl which may have one or more suitable substituent s) like phenyl(lower)alkoxycarbonyl which may have nitro or lower alkoxy [e.g. benzyloxycarbonyl, phenethyloxycarbonyl, p-nitrobenzyloxycarbonyl, p-methylbenzyloxycarbonyl, etc.], lower alkylsulfonyl [e.g. methylsulfonyl, ethylsulfonyl, propylsulfonyl, isopropylsulfonyl, pentylsulfonyl, butylsulfonyl, etc.], arylsulfonyl [e.g. phenylsulfonyl, naphthylsulfonyl, etc.] which may have one or more (preferably 1 to 3) suitable substituent(s) such as lower alkyl, higher alkoxy, or the like, ar(lower)alkylsulfonyl such as phenyl(lower)alkylsulfonyl [e.g. benzylsulfonyl, phenethylsulfonyl, benzhydrylsulfonyl, etc.], or the like, aroyl which may have one or more (preferably 1 to 5) suitable substituent(s) such as halogen, lower alkyl, higher alkyl, lower alkoxy which may have one or more (preferably 1 to 10) suitable substituent(s) such as lower alkoxy; halogen; aryl; or the like, higher alkoxy which may have one or more (preferably 1 to 17) suitable substituent(s) like halogen, or the like, and the like, in which the preferred one may be aroyl having higher alkoxy, aroyl substituted with heterocyclic group which has aryl having lower alkoxy, aroyl substituted with heterocyclic group which has aryl having higher alkoxy, ar(lower)alkenoyl substituted with aryl having lower alkoxy, ar(lower)alkenoyl substituted with aryl having higher alkoxy, aroyl substituted with aryl which has aryl having lower alkoxy, aroyl substituted with aryl which has aryl having higher alkoxy, aroyl substituted with heterocyclic group which has aryl. substituted with aryl having lower alkoxy, aroyl substituted with heterocyclic group which has aryl substituted with aryl having higher alkoxy.

Suitable example of "aroyl having higher alkoxy" may be benzoyl having $(C_7–C_{17})$alkoxy, in which the preferred one may be benzoyl having octyloxy.

Suitable example of "aroyl substituted with heterocyclic group which has aryl having lower alkoxy" may be benzoyl substituted with saturated 6-membered heteromonocyclic group containing 1 to 4 nitrogen atom(s) which has phenyl having $(C_4–C_6)$alkoxy, benzoyl substituted with unsaturated 5-membered heteromonocyclic group containing 1 to 2 sulfur atom(s) and 1 to 3 nitrogen atom(s) which has phenyl having $(C_4–C_6)$alkoxy, benzoyl substituted with unsaturated condensed heterocyclic group containing 1 to 2 sulfur atom (s) and 1 to 3 nitrogen atom(s) which has phenyl having $(C_4–C_6)$alkoxy or benzoyl substituted with unsaturated 5-membered heteromonocyclic group containing 1 to 2 oxygen atom(s) and 1 to 3 nitrogen atom(s) which has phenyl having $(C_4–C_6)$alkoxy, in which the preferred one may be benzoyl substituted with piperazinyl which has phenyl having $(C_4–C_6)$alkoxy, benzoyl substituted with thiadiazolyl which has phenyl having $(C_4–C_6)$alkoxy, benzoyl substituted with thiazolyl which has phenyl having $(C_4–C_6)$ alkoxy, benzoyl substituted with imidazothiadiazolyl which has phenyl having $(C_4–C_6)$alkoxy or benzoyl substituted with isoxazolyl which has phenyl having $(C_4–C_6)$alkoxy, and the most preferred one may be benzoyl substituted with piperazinyl which has phenyl having hexyloxy, benzoyl substituted with thiadiazolyl which has phenyl having hexyloxy, benzoyl substituted with thiazolyl which has phenyl having pentyloxy or hexyloxy, benzoyl substituted with imidazothiadiazolyl which has phenyl having pentyloxy or benzoyl substituted with isoxazolyl which has phenyl having pentyloxy.

Suitable example of "ar(lower)alkenoyl substituted with aryl having lower alkoxy" may be phenyl($C_3–C_6$)alkenoyl substituted with phenyl having $(C_4–C_6)$alkoxy, in which the preferred one may be phenylacryloyl substituted with phenyl having pentyloxy.

Suitable example of "aroyl substituted with aryl which has aryl having lower alkoxy" may be benzoyl substituted with phenyl which has phenyl having $(C_4–C_6)$alkoxy, in which the preferred one may be benzoyl substituted with phenyl which has phenyl having pentyloxy.

Suitable example of "aroyl substituted with heterocyclic group which has aryl substituted with aryl having lower alkoxy" may be benzoyl substituted with unsaturated 5-membered heteromonocyclic group containing 1 to 2 sulfur atom(s) and 1 to 3 nitrogen atom(s) which has phenyl substituted with phenyl having $(C_1–C_4)$alkoxy, in which the preferred one may be benzoyl substituted with thiadiazoyl which has phenyl substituted with phenyl having $(C_1–C_4)$ alkoxy or benzoyl substituted with thiazolyl which has phenyl substituted with phenyl having $(C_1–C_4)$alkoxy, and the most preferred one may be benzoyl substituted with thiadiazolyl which has phenyl substituted with phenyl having propoxy or benzoyl substituted with thiazoyl which has phenyl substituted with phenyl having propoxy.

The process for preparing the object compound [I] or a salt thereof of the present invention is explained in detail in the following.

Process 1

The object compound [Ia] or a salt thereof can be prepared by the fermentation process.

The fermentation process is explained in detail in the following.

The compound [Ia] or a salt thereof of this invention can be produced by fermentation of the compound [Ia] or a salt thereof-producing strain belonging to the genus Coleophoma such as *Coleophoma crateriformis* No.738 in a nutrient medium.

(i) Microorganism

Particulars of the microorganism used for producing the compound [Ia] or a salt thereof is explained in the following.

The fungus strain No.738 was originally isolated from a leaf sample, collected at Mt. Tateyama, Kaminiikawa-gun, Toyama-ken, Japan. This organism grew rather restrictedly on various culture media, and formed grayish colonies. The strain produced pycnidial conidiomata flattened at the base, on steam-sterilized leaf segments affixed on an agar medium by inoculating the isolate, while it formed neither teleo-morph nor anamorph on agar media. The conidiomata were discoid or sometimes papillate, dark brown to black, and formed conidiophores on the lower cells of its inner walls.

Conidiogenous cells were ampulliform to lageniform, and conidia were hyaline, one-celled, cylindrical. They were covered with thin-walled sheath. On the basis of comparing the morphological characteristics with fungal taxonomic criteria by von Arx (J.A. van Arx: The Genera of Fungi—Sporulating in Pure Culture. 3rd ed., pp.145–163, J. Cramer, Vaduz, 1974), strain No.738 was considered to belong to the coelomycete genus Coleophoma Höhn. 1907 (Sphaeropsidales). Its mycological characteristics were as follows.

Cultural characteristics on various agar media are summarized in Table 1. Culture on potato dextrose agar grew rather rapidly, attaining 3.0–4.0 cm in diameter two weeks later at 25° C. This colony surface was convex to raised, cottony and partly fasciate, sectoring, and showed several colors; pale gray to olive at the center, white to yellowish white at the margin and olive brown at the sectors. The colony margin was wet and lustrous. The reverse was yellowish gray, and olive gray at the sectors. Conidial structures were not observed. Colonies on corn meal agar grew rather restrictedly, attaining 2.5–3.5 cm in diameter under the same conditions. The surface was flat, felty and dark gray to olive gray. The colony margin was submerged, lustrous and olive. The reverse was black, and olive gray at the margin. Conidial structures were not produced.

The morphological characteristics were determined from the cultures on sterile leaf segments affixed on a Miura' LCA plate (Miura, K. and M. Kudo: Trans. Mycol. Soc. Japan, 11:116–118, 1970). Conidiomata formed on the leaf segments alone. They were pycnidial, superficial, separate, discoid or sometimes papillate none-ostiolate or indistinctly ostiolate, flattened at the base, unilocular, thick-walled textura angularis with thin upper wall, dark brown to black, 90–160 (–400) mm in diameter and 50–90 mm high. Conidiophores formed from the lower cells of inner pycnidial walls. The conidiophore-producing cells were hyaline, subglobose and 4–6 (–7.5) mm in diameter. The conidiophores were hyaline, smooth, septate, simple to sparingly branched, and 3–13.5×3–4 mm. They formed discrete conidiogenous cells at the apex. The conidiogenous cells were hyaline, smooth, ampulliform to lageniform, or cylindrical, and 4–8.5×2.5–4 mm. Conidia were hyaline, smooth, one-celled, cylindrical, rounded at the apical end, with a small projection at the base, and 10–13×2–3 mm. Both conidium and conidiogenous cell were covered with a large sheath. The sheaths were hyaline, thin-walled campanulate to cylindrical and 14–21.5×3–5 mm. Vegetative hyphae were smooth, septate, brown and branched. The hyphal cells were cylindrical, and 2–7 mm in width. Chlamydospores were not observed.

Strain No.738 was able to grow at the temperature range from 3 to 30° C. with the growth optimum at 20 to 24° C. These temperature data were determined on potato dextrose agar (made by NISSUI).

According to the taxonomic criteria of the genus Coleophoma by Sutton (B. C. Sutton: The Coelomycetes—Fungi Imperfecti with Pycnidia, Acervuli and Stroma, pp.401–403, Commonwealth Mycological Institute, Kew, 1980), the strain No.738 resembles *Coleophoma crateriformis* (Dur. & Mont.) Hohn. 1907. Moreover, the above characteristics corresponded with the description by Sutton, with a few exceptions: superficial, none-ostiolate or indistinctly ostiolate conidiomata and sheaths covering with conidiogenous cells and conidia. However, the latter characteristics, sheaths, were described as paraphyses by Sutton. Thus, we identified the strain as one strain of *Coleophoma crateriformis*, and named it *Coleophoma crateriformis* No.738. This strain has been deposited with the National Institute of Bioscience and Human-Technology, Agency of Industrial Science and Technology, (1–3, Higashi 1-chome, Tsukuba-shi, IBARAKI 305 JAPAN) as FERM BP-5796 (deposited date: Jan. 23, 1997).

TABLE 1

Cultural characteristics of strain No.738.

| Media | | Cultural characteristics |
|---|---|---|
| Malt extract agar* | G: | Rather restrictedly, 3.0–3.5 cm |
| | S: | Circular, flat, felty, exudate at the center, formed no anamorph, dark gray (1F1) to violet gray (16F2) at the center and yellowish white (4A2) to yellowish gray (4B2) at the margin |
| | R: | Dark gray (1F1) at the center and yellowish gray (4B2) to olive gray (4D3) at the margin |
| Potato dextrose agar (Difco 0013) | G: | Rather rapidly, 3.0–4.0 cm |
| | S: | Circular to irregular, convex to raised, cottony and partly fasciate, wet and lustrous at the margin, sectoring, formed no anamorph, pale gray (1B1) to olive (1F3) at the center, white to yellowish white (4A2) at the margin and olive brown (4F3) at the sectors |
| | R: | Yellowish gray (2B-C2), and olive gray (2F2) at the sectors |
| Czapek's solution agar* | G: | Very restrictedly, 0.5 cm |
| | S: | Irregular, scanty, flat, formed no anamorph, grayish brown (5F3) |
| | R: | Brownish gray (5F2) |
| Sabouraud dextrose agar (Difco 0190) | G: | Rather restrictedly, 3.0–3.5 cm |
| | S: | Circular, convex, felty and partly fasciate, wet, lustrous, sectoring, formed no anamorph, yellowish white (4A2), and grayish brown (5D-E3) at the center and sectors |
| | R: | Pale yellow (4A3), and olive brown (4D3) at the sectors |
| Emerson Yp Ss agar (Difco 0739) | G: | Restrictedly, 1.5–2.5 cm |
| | S: | Circular to irregular, flat to raised; felty, sulcate, sectoring, formed no anamorph, pale gray (1B1) to light gray (1D1), produced dark green soluble pigment |
| | R: | Olive (1-2F3), and yellowish gray (2D2) at the center |
| Corn meal agar (Difco 0386) | G: | Rather restrictedly, 2.5–3.5 cm |
| | S: | Circular, flat, felty, submerged at the margin, lustrous, formed no anamorph, dark gray (1F1) to olive gray (2F2), and olive (1E-F4) at the margin |
| | R: | Black, and olive gray (2E2) a the margin |
| MY20 agar* | G: | Rather restrictedly, 2.5–3.5 cm |
| | S: | Circular to irregular, flat, felty, wet, sectoring, formed no anamorph, olive brown (4D4-4F3), and grayish orange (6B3) at the center |
| | R: | Olive brown (4E4), and pale orange (5A3) at the center |
| Abbreviation | G: | growth, measuring colony size in diameter, |
| | S: | colony surface and |
| | R: | reverse. |

*The compositions of malt extract agar, Czapek's solution agar and MY20 agar were based on JCM Catalogue of Strains (Nakase, T., 5th ed., 503p., Japan Collection of Microorganisms and Life Science Research Information Section of the Institute of Physical and Chemical Research, Saitama, 1992).

These characteristics were observed after 14 days of incubation at 25° C. The color descriptions were based on Methuen Handbook of Colour (Kornerup, A. and J. H. Wanscher, 3rd ed., 525p., Methuen, London, 1978).

(ii) Production of the compound [Ia] or a salt thereof

The compound [Ia] or a salt thereof of this invention is produced when the compound [Ia] or a salt thereof-producing strain belonging to the genus Coleophoma is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, sucrose, starch, fructose or glycerin, or the like.

The preferred sources of nitrogen are yeast extract, peptone, gluten meal, cotton seed flour, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea or amino acid, or the like.

The carbon and nitrogen sources, though advantageously employed in combination, need not to be used in their pure form because less pure materials, which contain traces of growth factors and considerable guantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, zinc salts, or cobalt salts, or the like.

If necessary, especially when the culture medium foams seriously a defoaming agent, such as liquid paraffin, fatty oil, plant oil, mineral oil or silicone, or the like may be added.

As in the case of the preferred methods used for the production of other biologically active substances in massive amounts, submerged aerobic cultural conditions are preferred for the production of the compound [Ia] or a salt thereof in massive amounts.

For the production in small amounts, a shaking or surface culture in a flask or bottle is employed.

Further, when the growth is carried out in large tanks, it is preferable to use the vegetative form of the organism for inoculation in the production tanks in order to avoid growth lag in the process of production of the compound [Ia] or a salt thereof. Accordingly, it is desirable first to produce a vegetative inoculum of the organism by inoculating a relatively small quantity of culture medium with spores or mycelia of the organism and culturing said inoculated medium, and then to transfer the cultured vegetative inoculum to large tanks. The medium, in which the vegetative inoculum is produced, is substantially the same as or different from the medium utilized for the production of the compound [Ia] or a salt thereof.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 10° C. and 40° C., preferably 20° C. to 30° C., for a period of about 50 hours to 150 hours, which may be varied according to fermentation conditions and scales.

When the fermentation is completed, the culture broth is then subjected for recovery of the compound [Ia] or a salt thereof to various procedures conventionally used for recovery and purification of biological active substances, for instance, solvent extraction with an appropriate solvent or a mixture of some solvents, chromatography or recrystallization from an appropriate solvent or a mixture of some solvents, or the like.

According to this invention, in general, the compound [Ia] or a salt thereof is found both in the cultured mycelia and cultured broth. Accordingly, then the compound [Ia] or a salt thereof is removed from the whole broth by means of extraction using an appropriate organic solvent such as acetone or ethyl acetate, or a mixture of these solvent, or the like.

The extract is treated by a conventional manner to provide the compound [Ia] or a salt thereof, for example, the extract is concentrated by evaporation or distillation to a smaller amount and the resulting residue containing active material, i.e. the compound [Ia] or a salt thereof is purified by conventional purification procedures, for example, chromatography on recrystallization from an appropriate solvent or a mixture of some solvents.

When the object compound is isolated as a salt of the compound [Ia], it can be converted to the free compound [Ia] or another salt of the compound [Ia] according to a conventional manner.

Process 2

The object polypeptide compound [Ib] or a salt thereof can be prepared by subjecting a compound [Ia] or a salt thereof to elimination reaction of N-acyl group.

This reaction is carried out in accordance with a conventional method such as hydrolysis, reduction, reaction with an enzyme or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2] octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.], or the like, is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [eg.. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts

[e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

The reaction with an enzyme can be carried out by reacting the compound [Ia] or a salt thereof with an enzyme suitable for the elimination reaction of N-acyl group.

Suitable example of said enzyme may include the one produced by certain microorganisms of the Streptomycetaceae, the Actinoplanaceae, the Oidiodendron or the Verticillium, for example, Streptomyces sp. No.6907 (FERM BP-5809), *Streptomyces anulatus* No.4811 (FERM BP-5808), *Streptomyces anulatus* No.8703 (FERM BP-5810), *Actinoplanes utahensis* IFO-13244, *Actinoplanes utahensis* ATCC 12301, *Actinoplanes missenrienses* NRRL 12053, Oidiodendron sp. No.30084 (FERM P-15550), Verticillium sp. No.30085 (FERM P-15551), or the like; and the like.

This elimination reaction is usually carried out in a solvent such as phosphate buffer, Tris-HCl buffer or any other solvent which does not adversely influence the reaction.

The reaction temperature is not critical and the reaction can be carried out at room temperature or under warming.

Process 3

The object polypeptide compound [Ic] or a salt thereof can be prepared by reacting the compound [Ib] or its reactive derivative at the amino group or a salt thereof with the compound [III] or its reactive derivative at the carboxy group or a salt thereof.

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g., methanesulfonic acid, etc.], aliphatic carboxylic acid [e.g., acetic acid, propionic acid, butyric acid, isobutyric acid, pivaric acid, pentanoic acid, isopentanoic acid, 2-ethylbutyric acid, trichloroacetic acid, etc.]; or aromatic carboxylic acid [e.g., benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl

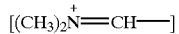

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the mind of the compound [III] to be used.

Suitable salts of the compound [III] and its reactive derivative can be referred to the ones as exemplified for the object polypeptide compound [I].

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide, N,N-carbonylbis-(2-methylimidazole); pentamethyleneketene-N-cyclohexylimine; diphenylketene-N-cyclohexylimine; ethoxyacetylene; 1-alkoxy-2-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorous oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, di(lower)alkylaminopyridine (e.g., 4-dimethylaminopyridine, etc.), N-(lower)alkylmorpholine, N,N-di(lower)alkylbenzylamine, or the like.

The reaction temperature is not critical, and the reaction is usually carried out under cooling to warming.

The compounds obtained by the above Processes 1 to 3 can be isolated and purified by a conventional method such as pulverization, recrystallization, column-chromatography, high-performance liquid chromatography (HPLC), reprecipitation, or the like.

The compounds obtained by the above Processes 1 to 3 may be obtained as its hydrate, and its hydrate is included within the scope of this invention.

BIOLOGICAL PROPERTY OF THE POLYPEPTIDE COMPOUND [I] OF THE PRESENT INVENTION

In order to show the usefulness of the polypeptide compound [I] of the present invention, the biological data of the representative compound is explained in the following.

Test (Antimicrobial Activity)
Test Method

Antimicrobial activity of the object compounds of Examples 1 and 2 were determined by a serial broth dilution method using 96-well microtiter plate in 100 µl of MEM (Eagle's minimum essential medium) for *Candida albicans* and in 100 µl of yeast nitrogen base dextrose medium for *Aspergillus fumigatus*. The inoculum was adjusted to 1×10$^5$ colony forming units/ml. *Candida albicans* and *Asperaillus fumigatus* were cultured at 37° C. for 24 hours in 5% $CO_2$ incubator. After incubation, the growth inhibition of microorganisms in each well was determined by microscopic observation. The results were shown as MEC (minimum effective concentration : µg/ml) value (Table 2).

Test Result

TABLE 2

| Test compound Microorganisms | [MEC (µg/ml)] | | |
|---|---|---|---|
| | WF 738A | WF 738C | WF 738B |
| *Candida albicans* FP633 | 0.04 | 0.04 | 0.04 |
| *Aspergillus fumigatus* FP1305 | 0.04 | 0.04 | 0.04 |

From the test result, it is realized that the object polypeptide compound [I] of the present invention has an antimicrobial activity (especially, antifungal activity).

The pharmaceutical composition of the present invention can be used in the form of a pharmaceutical preparation, for example, in solid, semisolid or liquid form, which contains the object polypeptide compound [I] or a pharmaceutically acceptable salt thereof, as an active ingredient in admixture with an organic or inorganic carrier or excipient which is suitable for rectal; pulmonary (nasal or buccal inhalation); ocular; external (topical); oral administration; parenteral (including subcutaneous, intravenous and intramuscular) administrations; insufflation (including aerosols from metered dose inhalator); nebulizer; or dry powder inhalator.

The active ingredient may be compounded, for example, with the usual non-toxic, pharmaceutically acceptable carriers in a solid form such as granules, tablets, dragees, pellets, troches, capsules, or suppositories; creams; ointments; aerosols; powders for insufflation; in a liquid form such as solutions, emulsions, or suspensions for injection; ingestion; eye drops; and any other form suitable for use. And, if necessary, there may be included in the above preparation auxiliary substance such as stabilizing, thickening, wetting, emulsifying and coloring agents; perfumes or buffer; or any other commonly may be used as additives.

The object polypeptide compound [I] or a pharmaceutically acceptable salt thereof is/are included in the pharmaceutical composition in an amount sufficient to produce the desired antimicrobial effect upon the process or condition of diseases.

For applying the composition to human, it is preferable to apply it by intravenous, intramuscular, pulmonary, oral administration, or insufflation. While the dosage of therapeutically effective amount of the object polypeptide compound [I] varies form and also depends upon the age and condition of each individual patient to be treated, in the case of intravenous administration, a daily dose of 0.01–20 mg of the object polypeptide compound [I] per kg weight of human being in the case of intramuscular administration, a daily dose of 0.1–20 mg of the object polypeptide compound [I] per kg weight of human being, in case of oral administration, a daily dose of 0.5–50 mg of the object polypeptide compound [I] per kg weight of human being is generally given for treating or preventing infectious diseases.

Especially in case of the treatment of prevention of *Pneumocystis carinii* infection, the followings are to be noted.

For administration by inhalation, the compounds of the present invention are conveniently delivered in the form of an aerosol spray presentation from pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol administration is a preferred method of administration. Insufflation is also a desirable method, especially where infection may have spread to ears and other body cavities.

Alternatively, parenteral administration may be employed using drip intravenous administration.

The following Preparations and Examples are given for the purpose of illustrating the present invention in more detail.

Preparation 1

To a solution of 2-amino-4'-bromoacetophenone hydrochloride (8.2 g), 4-pentyloxybenzoic acid (6.8 g) and 1-hydroxybenzotriazole (4.42 g) in dichloromethane (80 ml) was added 1-ethyl-3-(3'-dimethylaminopropyl)carbodiimide (WSCD) (6.0 ml), and stirred for 3 hours at ambient temperature. The reaction mixture was diluted with dichloromethane (800 ml), and washed with 1N hydrochloric acid, saturated sodium hydrogen carbonate aqueous solution and brine. The organic layer was dried over magnesium sulfate. Magnesium sulfate was filtered off, and the filtrate was evaporated under reduced pressure. The solids were slurried in ethyl acetate, and collected by filtration to give 2-(4-pentyloxybenzamido)-4'-bromoacetophenone (2.49 g).

NMR (DMSO-$d_6$, δ): 0.80–1.00 (3H, m), 1.22–1.55 (4H, m), 1.60–1.85 (2H, m), 4.03 (2H, t, J=6.5 Hz), 4.72 (2H, d, J=5.6 Hz), 7.01 (2H, d, J=8.8 Hz), 7.78 (2H, d, J=8.5 Hz), 7.85 (2H, d, J=8.8 Hz), 7.97 (2H, d, J=8.6 Hz), 8.72 (1H, t, J=5.6 Hz)

MASS (m/z): 404, 406

Preparation 2

To a solution of 2-(4-pentyloxybenzamido)-4'-bromoacetophenone (3.39 g) in tetrahydrofuran (34 ml) was added phosphorus pentasulfide (2.43 g), and refluxed for 30 minutes. The reaction mixture was cooled, and poured into saturated sodium hydrogen carbonate aqueous solution (400 ml), and stirred for 1.5 hours. The resulting precipitate was collected by filtration to give 2-(4-pentyloxyphenyl)-5-(4-bromophenyl)thiazole (2.32 g).

IR (KBr): 2939.0, 2858.0, 1602.6, 1525.4, 1473.3, 1257.4 cm$^{-1}$

NMR (CDCl$_3$, δ): 0.80–1.00 (3H, m), 1.25–1.60 (4H, m), 1.70–1.95 (2H, m), 4.01 (2H, t, J=6.5 Hz), 6.96 (2H, d, J=8.9 Hz), 7.44 (2H, d, J=8.8 Hz), 7.54 (2H, d, J=8.8 Hz), 7.90 (2H, d, J=8.9 Hz), 7.95 (1H, s)

MASS (m/z): 402, 404

Preparation 3

A solution of 2-(4-pentyloxyphenyl)-5-(4-bromophenyl) thiazole (2.3 g) in dry tetrahydrofuran (60 ml) was cooled to −60° C., and a solution of n-butyllithium (1.66M in n-hexane, 4.46 ml) was added slowly to maintain the reaction temperature at −60° C. After stirring for 1 hour, a solution of n-butyllithium (1.66M in n-hexane, 1.0 ml) was additionally added. The reaction mixture was allowed to warm to −40° C. After stirring for 30 minutes, dry-ice (5 g) was added. The reaction mixture was allowed to warm to room temperature over 30 minutes. To the reaction mixture was added water (25 ml) and 0.5N-hydrochloric acid (100 ml), then extracted with dichloromethane (500 ml). The organic layer was washed with brine, and dried over magnesium sulfate. Magnesium sulfate was filtered off, and the filtrate was evaporated under reduced pressure. The solids were slurried in acetonitrile, and collected by filtration to give 4-[2-(4-pentyloxyphenyl)thiazol-5-yl]benzoic acid (1.70 g).

IR (KBr): 2954.4, 2867.6, 2667.1, 2547.5, 1683.6, 1604.5, 1430.9, 1295.9, 1253.5 cm$^{-1}$

NMR (DMSO-$d_6$, δ): 0.80–1.00 (3H, m), 1.20–1.55 (4H, m), 1.60–1.85 (2H, m), 4.04 (2H, t, J=6.5 Hz), 7.07 (2H, d, J=8.8 Hz), 7.83 (2H, d, J=8.4 Hz), 7.91 (2H, d, J=8.8 Hz), 8.01 (2H, d, J=8.4 Hz), 8.39 (1H, s)

MASS (m/z): 368

Preparation 4

To a solution of 1-hydroxybenzotriazole (722 mg) and 4-[2-(4-pentyloxyphenyl)thiazol-5-yl]benzoic acid (1.64 g) in dichloromethane (33 ml) was added 1-ethyl-3-(3'-dimethylaminopropyl)carbodiimide hydrochloride (WSC.HCl) (1.28 g), and stirred for 2 hours at ambient temperature. To the reaction mixture was added dichloromethane (500 ml) to be clear solution, then washed with water (200 ml×2) and brine, and dried over magnesium sulfate. Magnesium sulfate was filtered off, and the filtrate was evaporated under reduced pressure. The solids were slurried in acetonitrile, and collected by filtration to give 4-[2-(4-pentyloxyphenyl)-thiazol-5-yl]benzoic acid benzotriazol-1-yl ester (1.27 g).

IR (KBr): 3461.6, 2948.6, 2869.6, 1781.9, 1602.6, 1261.2, 985.4 cm$^{-1}$

NMR (CDCl$_3$, δ): 0.90–1.05 (3H, m), 1.30–1.60 (4H, m), 1.70–1.95 (2H, m), 4.03 (2H, t, J=6.5 Hz), 6.99 (2H, d, J=8.9 Hz), 7.40–7.70 (3H, m), 7.82 (2H, d, J=8.6 Hz), 7.94 (2H, d, J=8.9 Hz), 8.12 (2H, d, J=8.1 Hz), 8.17 (1H, s), 8.31 (2H, d, J=8.6 Hz)

MASS (m/z): 485

The following compound was obtained according to a similar manner to that of Preparation 1.

Preparation 5

2-(4-Hexyloxybenzamido)-4'-bromoacetophenone

IR (KBr): 3317.0, 2937.1, 2867.6, 1699.0, 1637.3, 1556.3, 1508.1, 1253.5 cm$^{-1}$

NMR (DMSO-$d_6$, δ): 0.80–1.00 (3H, m), 1.20–1.55 (6H, m), 1.60–1.85 (2H, m), 4.03 (2H, t, J=6.4 Hz), 4.72 (2H, d, J=5.5 Hz), 7.01 (2H, d, J=8.8 Hz), 7.77 (2H, d, J=8.6 Hz), 7.85 (2H, d, J=8.8 Hz), 7.97 (2H, d, J=8.6 Hz), 8.72 (1H, t, J=5.6 Hz)

MASS (m/z): 418, 420

The following compound was obtained according to a similar manner to that of Preparation 2.

Preparation 6

2-(4-Hexyloxyphenyl)-5-(4-bromophenyl)thiazole

IR (KBr): 2937.1, 2854.1, 1602.6, 1523.5, 1475.3, 1438.6, 1255.4, 833.1 cm$^{-1}$

NMR (CDCl$_3$, δ): 0.80–1.10 (3H, m), 1.20–1.60 (6H, m), 1.70–1.95 (2H, m), 4.01 (2H, t, J=6.5 Hz), 6.96 (2H, d, J=8.9 Hz), 7.44 (2H, d, J=8.7 Hz), 7.54 (2H, d, J=8.7 Hz), 7.89 (2H, d, J=8.9 Hz), 7.94 (1H, s)

MASS (m/z): 416, 418

The following compound was obtained according to a similar manner to that of Preparation 3.

Preparation 7

4-[2-(4-Hexyloxyphenyl)thiazol-5-yl]benzoic acid

IR (KBr): 2933.2, 2863.8, 2669.0, 2547.5, 1679.7, 1604.5, 1513.8, 1432.9, 1297.9, 1251.6 cm$^{-1}$

NMR (DMSO-$d_6$, δ): 0.80–1.00 (3H, m), 1.15–1.60 (6H, m), 1.60–1.85 (2H, m), 4.05 (2H, t, J=6.5 Hz), 7.07 (2H, d, J=8.8 Hz), 7.83 (2H, d, J=8.4 Hz), 7.91 (2H, d, J=8.8 Hz), 8.01 (2H, d, J=8.4 Hz), 8.40 (1H, S)

MASS (m/z): 382

The following compounds [Preparation 8 to 10] were obtained according to a similar manner to that of Preparation 4.

Preparation 8

4-[2-(4-Hexyloxyphenyl)thiazol-5-yl]benzoic acid benzotriazol-1-yl ester

IR (KBr): 2927.4, 2865.7, 1774.2, 1602.6, 1434.8, 1251.6, 1187.9, 993.2 cm$^{-1}$

NMR (CDCl$_3$, δ): 0.85–1.05 (3H, m), 1.20–1.60 (6H, m), 1.60–1.95 (2H, m), 4.03 (2H, t, J=6.5 Hz), 6.99 (2H, d, J=8.8 Hz), 7.35–7.70 (3H, m), 7.81 (2H, d, J=8.5 Hz), 7.94 (2H, d, J=8.8 Hz), 8.12 (2H, d, J=8.1 Hz), 8.17 (1H, s), 8.31 (2H, d, J=8.5 Hz)

MASS (m/z): 499

Preparation 9

4-[5-(4-Hexyloxyphenyl)thiazol-2-yl]benzoic acid benzotriazol-1-yl ester

IR (KBr): 2946.7, 2865.7, 1776.1, 1604.5, 1251.6, 1230.4 cm$^{-1}$

NMR (CDCl$_3$, δ): 0.80–1.05 (3H, m), 1.20–1.65 (6H, m), 1.70–1.95 (2H, m), 4.01 (2H, t, J=6.5 Hz), 6.97 (2H, d, J=8.8 Hz), 7.40–7.65 (5H, m), 8.03 (1H, s), 8.12 (1H, d, J=8.2 Hz), 8.18 (2H, d, J=8.7 Hz), 8.36 (2H, d, J=8.7 Hz)

MASS (m/z): 499

Preparation 10

4-[5-[4-(4-Propoxyphenyl)phenyl]thiazol-2-yl]benzoic acid benzotriazol-1-yl ester IR (KBr): 2967.9, 2937.1, 2875.3, 1772.3, 1600.6, 1249.6 cm$^{-1}$ NMR (CDCl$_3$, δ): 1.07 (3H, t, J=7.4 Hz), 1.75–1.95 (2H, m), 3.99 (2H, t, J=6.6 Hz), 7.01 (2H, d, J=8.7 Hz), 7.40–7.60 (3H, m), 7.60 (2H, d, J=8.7 Hz), 7.69 (2H, d, J=8.4 Hz), 7.85 (2H, d, J=8.5 Hz), 8.06 (2H, d, J=8.4 Hz), 8.13 (2H, d, J=8.1 Hz), 8.24 (1H, s), 8.34 (2H, d, J=8.5 Hz)

MASS (m/z): 533

Preparation 11

To a solution of 2-amino-4'-methoxyacetophenone hydrochloride (5.33 g) in pyridine (4.28 ml), triethylamine (3.68 ml) and dichloromethane (50 ml) was added dropwise a solution of terephthalic acid monomethyl ester (5.25 g) in dichloromethane (10 ml) at 0° C. The reaction mixture was allowed to warm to room temperature, and stirred for 3 hours. To the reaction mixture was added dichloromethane (200 ml), washed with 1N-sodium hydroxide (100 ml×2), saturated hydrogen carbonate aqueous solution (100 ml×2) and brine, and dried over magnesium sulfate. Magnesium sulfate was filtered off, and the filtrate was evaporated under reduced pressure. The solids were slurried in n-hexane, and collected by filtration to give 2-(4-methoxycarbonyl-benzamido)-4'-methoxyacetophenone (7.97 g).

IR (KBr): 3401.8, 3378.7, 2956.3, 2844.5, 1724.0, 1683.6, 1643.1, 1602.6, 1290.1, 1263.1 cm$^{-1}$

NMR (CDCl$_3$, δ): 3.91 (3H, s), 3.96 (3H, s), 4.91 (2H, d, J=4.1 Hz), 7.00 (2H, d, J=8.9 Hz), 7.40 (1H, t, J=4.1 Hz), 7.94 (2H, d, J=8.6 Hz), 8.02 (2H, d, J=8.9 Hz), 8.14 (2H, d, J=8.6 Hz)

MASS (m/z): 328

Preparation 12

To a solution of 2-(4-methoxycarbonylbenzamido)-4'-methoxyacetophenone (4.0 g) in tetrahydrofuran (80 ml) was added phosphorus pentasulfide (3.53 g), and refluxed for 2.5 hours. The reaction mixture was additionally added phosphorus pentasulfide (1.0 g), and refluxed for 1 hour. The reaction mixture was filtered, and the filtrate was cooled, and poured into water (1200 ml), and stirred for 1 hour. The resulting precipitate was collected by filtration. The solids were slurried in acetonitrile, and collected by filtration to give methyl 4-[5-(4-methoxyphenyl)thiazol-2-yl]benzoate (3.26 g).

IR (KBr): 2950.6, 2840.6, 1712.5, 1604.5, 1280.5, 1249.6 cm$^{-1}$

NMR (CDCl$_3$, δ): 3.86 (3H, s), 3.95 (3H, s), 6.96 (2H, d, J=8.8 Hz), 7.55 (2H, d, J=8.8 Hz), 7.97 (1H, s), 8.02 (2H, d, J=8.7 Hz), 8.12 (2H, d, J=8.7 Hz)

MASS (m/z): 326

Preparation 13

To a solution of boron tribromide (1.0M in dichloromethane, 97.7 ml) was added dropwise methyl 4-[5-(4-methoxyphenyl)thiazol-2-yl]benzoate (3.18 g) in dichloromethane (50 ml) at −78° C. The reaction mixture was allowed to warm to room temperature, and stirred for 2 hours. The reaction mixture was poured into ice-water (1000 ml), and stirred for 30 minutes at room temperature. The precipitate was collected by filtration, washed with water, and dried overnight to give in the proportion of 37:63 mixture of methyl 4-[5-(4-hydroxyphenyl)thiazol-2-yl] benzoate and 4-[5-(4-hydroxyphenyl)thiazol-2-yl]benzoic acid (3.07 g), and those were used without purification in the next reaction.

Preparation 14

To a suspension of a mixture of methyl 4-[5-(4-hydroxyphenyl)thiazol-2-yl]benzoate and 4-[5-(4-hydroxyphenyl)thiazol-2-yl]benzoic acid (1.0 g), potassium carbonate (930 mg) in N,N-dimethylformamide (5 ml) was added n-hexylbromide (0.95 ml), and stirred at 100° C. (bath temperature). After 3.5 hours, to the reaction mixture was additionally added n-hexylbromide (0.25 ml), and stirred at 100° C. (bath temperature) for 1 hour. After cooling, the mixture was added to 0.1N hydrochloric acid (100 ml). The resulting precipitate was collected by filtration, washed with water, and dried overnight. To this material was added the solution of tetrahydrofuran (20 ml), methanol (20 ml) and 10% sodium hydroxide aqueous solution (2.5 ml). The mixture was refluxed for 2 hours. After cooling, the reaction mixture was diluted with water (100 ml), and adjusted to pH 2 with 1N hydrochloric acid. The resulting precipitate was collected by filtration. The solid was collected by filtration, washed with water and acetonitrile, and dried to give 4-[5-(4-hexyloxyphenyl)thiazol-2-yl]benzoic acid (621 mg).

IR (KBr): 2933.2, 2865.7, 2661.3, 2539.8, 1681.6, 1604.5, 1430.9, 1288.2, 1251.6 cm$^{-1}$

NMR (CDCl$_3$, δ): 1.80–1.00 (3H, m), 1.20–1.60 (6H, m), 1.60–1.85 (2H, m), 4.02 (2H, t, J=6.5 Hz), 7.04 (2H, d, J=8.8 Hz), 7.67 (2H, d, J=8.8 Hz), 8.06 (4H, s), 8.28 (1H, s), 13.20 (1H, br s)

MASS (m/z): 382

Preparation 15

To a solution of 4'-ethoxycarbonyl-2-bromoacetophenone (2.0 g) in N,N-dimethylformamide (8 ml) was added sodium azide (480 mg) at 0° C., and stirred for 2 hours at room temperature. The reaction mixture was poured into water (100 ml), extracted with diethyl ether (200 ml×2), washed with brine, and dried over magnesium sulfate. Magnesium sulfate was filtered off, and the filtrate was evaporated under reduced pressure. The product was purified by silica gel column chromatography (ethyl acetate:hexane=1:5) to give 2-azido-4'-ethoxycarbonylacetophenone (1.46 g).

IR (KBr): 2991.1, 2904.3, 2104.0, 1702.8, 1288.2 cm$^{-1}$

NMR (CDCl$_3$, δ): 1.42 (3H, t, J=7.1 Hz), 4.42 (2H, q, J=7.1 Hz), 4.60 (1H, s), 7.96 (2H, d, J=8.7 Hz), 8.17 (2H, d, J=8.7 Hz)

MASS (m/z): 206

Preparation 16

To a solution of 2-azido-4'-ethoxycarbonylactophenone (1.44 g), methanol (41.3 ml) and conc. hydrochloric acid (1.38 ml) was added 10% palladium-activated carbon (73 mg), and stirred for 3 hours in hydrogen atmosphere at 2.8 atm. After 1 hour, the reaction mixture was filtered off, and the filtrate was evaporated under reduced pressure. The solids were slurried in diisopropyl ether, and collected by filtration to give 2-amino-4'-ethoxycarbonylacetophenone hydrochloride (1.40 g).

NMR (CDCl$_3$, δ): 1.35 (3H, t, J=7.1 Hz), 4.37 (2H, q, J=7.1 Hz), 4.65 (2H, s), 8.12 (2H, d, J=9.0 Hz), 8.17 (2H, d, J=9.0 Hz)

MASS (m/z): 208

Preparation 17

To a solution of 2-amino-4'-ethoxycarbonylacetophenone hydrochloride (700 mg), 4-(4-propoxyphenyl)benzoic acid (866 mg) and 1-hydroxybenzotriazole (456.5 mg) in triethylamine (0.47 ml) and dichloromethane (7 ml) was added 1-ethyl-3-(3'-dimethylaminopropyl)carbodiimide hydrochloride (WSC.HCl) (648 mg), and stirred for 5 hours at ambient temperature. To the reaction mixture was added water (100 ml), and extracted with dichloromethane. The organic layer was washed with 1N hydrochloric acid, water, saturated sodium hydrogen carbonate aqueous solution and brine. Then the organic layer was dried over magnesium sulfate. Magnesium sulfate was filtered off, and the filtrate was evaporated under reduced pressure. The solids were slurried in ethyl acetate, and collected by filtration to give 2-[4-(4-propoxyphenyl)benzoylamino]-4'-ethoxycarbonylacetophenone (746 mg).

IR (KBr): 3320.8, 2966.0, 2931.3, 2875.3, 1718.3, 1699.0, 1645.0, 1606.4, 1280.5 cm$^{-1}$

NMR (DMSO-d$_6$, δ): 1.00 (3H, t, J=7.4 Hz), 1.35 (3H, t, J=7.1 Hz), 1.76 (2H, q, J=7.3 Hz), 3.99 (2H, t, J=6.5 Hz), 4.36 (2H, q, J=7.1 Hz), 4.82 (1H, d, J=5.6 Hz), 7.05 (2H, d, J=8.8 Hz), 7.69 (2H, d, J=8.8 Hz), 7.76 (2H, d, J=8.4 Hz), 7.96 (2H, d, J=8.4 Hz), 8.11 (2H, d, J=8.7 Hz), 8.18 (2H, d, J=8.7 Hz), 8.97 (1H, t, J=5.6 Hz)

MASS (m/z): 446

Preparation 18

To a solution of 2-[4-(4-propoxyphenyl)benzoylamino]-4'-ethoxycarbonylacetophenone (709.4 mg) in tetrahydrofuran (7 ml) was added phosphorus pentasulfide (460 mg), and refluxed for 2 hours and 45 minutes. The reaction mixture was poured into ice-water (500 ml), neutralized by saturated sodium hydrogen carbonate aqueous solution, and stirred for 1 hour. The resulting precipitate was collected by filtration. The solids were slurried in acetonitrile, and collected by filtration to give ethyl 4-[2-(4'-propoxy-4-biphenyl)thiazol-5-yl]benzoate (481 mg).

IR (KBr): 2967.9, 2875.3, 1710.6, 1604.5, 1280.5 cm$^{-1}$

MASS (m/z): 444

Preparation 19

To a solution of ethyl 4-[2-(4'-propoxy-4-biphenyl)-thiazol-5-yl]benzoate (461.4 mg) in dichloromethane (20 ml), tetrahydrofuran (4 ml) and ethanol (200 ml) was added 10% sodium hydroxide aqueous solution (6.1 ml), and refluxed for 30 minutes. To the reaction mixture was added water (100 ml), and refluxed for 10 minutes. After cooling, the reaction mixture was adjusted to pH 2 with 1N hydrochloric acid. The resulting precipitate was collected by filtration, and washed with water. The solids were slurried in acetonitrile, and collected by filtration to give 4-[2-(4'-propoxy-4-biphenyl)thiazol-5-yl]benzoic acid (350 mg).

IR (KBr): 3455.8, 2966.0, 2877.3, 2676.7, 2551.4, 1685.5, 1604.5, 1432.9, 1286.3, 1253.5 cm$^{-1}$

NMR (DMSO-d$_6$, $\delta$): 1.00 (3H, t, J=7.4 Hz), 1.65–1.90 (2H, m), 3.99 (2H, t, J=6.5 Hz), 7.06 (2H, d, J=8.8 Hz), 7.76 (2H, d, J=8.5 Hz), 7.87 (2H, d, J=8.5 Hz), 8.02 (2H, d, J=8.5 Hz), 8.04 (2H, d, J=8.5 Hz), 8.49 (1H, s)

MASS (m/z): 416

EXAMPLE 1

(1) Fermentation

The seed medium (30 ml) consisting of sucrose 4%, glucose 1%, soluble starch 2%, cotton seed flour 3%, soybean powder 1.5%, KH$_2$PO$_4$ 1%, CaCO$_3$ 0.2%, Adekanol LG-109 (Asahi Denka Co., Ltd.) 0.05% and Silicone KM-70 (Shin-Etsu Chemical Co., Ltd.) 0.05% was poured into a 100 ml-Erlenmeyer flask and sterilized at 121° C. for 30 minutes. A loopful of slant culture of *Coleophoma crateriformis* No. 738 was inoculated to the medium and cultured at 25° C. for 5 days on a rotary shaker.

Four 8 ml portions of the seed culture were transferred to four 500 ml-Erlenmeyer flasks each containing 160 ml of the same seed medium, and cultured at 25° C. for 2 days on a rotary shaker (220 rpm, 5.1 cm-throw).

The resultant second seed culture was inoculated to a medium (20 l) consisting of modified starch 3%, starch acid hydrolysates 6%, cotton seed flour 1%, chicken meat bone meal 1%, dried yeast 2%, (NH$_4$)$_2$SO$_4$ 0.05%, NaH$_2$PO$_4$.12H$_2$O 0.5%, β-cyclodextrin 1%, Adekanol LG-109 0.05% and Silicone KM-70 0.05% in a 30 l-jar fermentor, which had been sterilized at 121° C. for 30 minutes in advance, and cultured at 25° C. for 4 days under aeration of 20 l/min. (internal pressure: 1 kg/cm$^2$) and agitation of 250 rpm.

The production of active compound in the fermentation broth was monitored by HPLC analysis.

(2) Isolation and Purification

After the culture was completed, an equal volume of acetone was added to the cultured broth (20 l). The mixture was allowed to stand for about an hour with stirring at room temperature. The resultant mixture was filtered with an aid of diatomaceous earth, yielding about 35 l of the filtrate. The filtrate was concentrated in vacuo to an aqueous solution and passed through a column (1 l) of Diaion HP-20 (Mitsubishi Chemical Co., Ltd.) packed with water. The column was washed with water (3 l) and 50% aqueous methanol (3 l) and then eluted with methanol (3 l). The eluate was concentrated in vacuo to give residual water. This residue was extracted twice with an equal volume of ethyl acetate. The aqueous layer was passed through a column (100 ml) of YMC GEL (ODS-AM 120-S50, YMC Co., Ltd.) packed with water. The column was washed with 20% aqueous acetonitrile containing 0.5% NaH$_2$PO$_4$.2H$_2$O (300 ml) and 40% aqueous acetonitrile containing 0.5% NaH$_2$PO$_4$.2H$_2$O (300 ml) and then eluted with 50% aqueous acetonitrile containing 0.5% NaH$_2$PO$_4$.2H$_2$O (200 ml). The eluate was concentrated in vacuo to an aqueous solution. This residue was passed through a column (20 ml) of Diaion HP-20 packed with water. The column was washed with water (200 ml) and then eluted with 80% aqueous methanol (60 ml). The eluate was concentrated in vacuo to an aqueous solution. This residue was applied onto a column (175 ml) or YMC GEL ODS-AM 120-S50 packed with water, and the column was eluted with 45% aqueous acetonitrile containing 0.5% NaH$_2$PO$_4$.2H$_2$O. Fractions containing the WF 738A and the WF 738C were combined and concentrated in vacuo respectively. The WF 738A and the WF 738C were finally purified by preparative HPLC, using a YMC-packed column (ODS-AM SH-343 5AM S-5 (YMC Co., Ltd., 250 mm L.×20 mm I.D.), with 55% aqueous acetonitrile containing 0.5% NaH$_2$PO$_4$.2H$_2$O as a mobile phase and flow rate of 9.9 ml/min.).

The portion corresponding to the WF 738A was concentrated in vacuo to give residual water. This residue was passed through a column (10 ml) of Diaion HP-20 packed with water. The column was washed with water (100 ml) and eluted with 80% aqueous methanol (30 ml). The eluate was concentrated and lyophilized to give 22 mg of the WF 738A as a white powder.

The portion corresponding to the WF 738C was concentrated in vacuo to give residual water. This residue was passed through a column (2 ml) of Diaion HP-20 packed with water. The column was washed with water (20 ml) and eluted with 80% aqueous methanol (6 ml). The eluate was concentrated and lyophilized to give 4 mg of the WF 738C as a white powder.

The WF 738A as obtained has the following physicochemical properties.

HPLC Condition
  Column: YMC Pack ODS-AM303 (250 mm L.×4.6 mm I.D.; YMC Co., Ltd.)
  Eluent: 55% acetonitrile–0.5% NaH$_2$PO$_4$.2H$_2$O
  Flow rate: 1 ml/min
  Detection: UV at 210 nm
  Retention time: 8.1 minutes Appearance
  white powder Nature
  acid substance Molecular Formula
  C$_{50}$H$_{79}$N$_8$O$_{20}$SNa [free acid: C$_{50}$H$_{80}$N$_8$O$_{20}$S]

Molecular Weight
  Molecular weight: 1144 (free acid)
  ESI-MS: (m/z) 1145 (M+H)$^+$ Elementary Analysis
  Calcd. for C$_{50}$H$_{79}$N$_8$O$_{20}$SNa.6H$_2$O C, 47.09; H, 7.19; N, 8.79; S, 2.51; (%)
  Found: C, 47.23, H, 7.35; N, 8.56; S, 2.18; (%)

Melting Point
  173–177° C. (dec.)

Specific Rotation
  $[\alpha]_D^{23}$ –10° (C 0.5, methanol)

Ultraviolet Absorption Spectrum
  $\lambda_{max}^{methanol}$: 278 nm ($\epsilon$1487)

Solubility
  Soluble: water, methanol, dimethylsulfoxide
  Insoluble: chloroform Color Reaction
  Positive: iodine vapor reaction, ceric sulfate reaction
  Negative: ninhydrin reaction, Molish reaction, Dragendorff reaction, ferric chloride reaction Thin Layer Chromatography (TLC)

| Stationary phase | Developing solvent | Rf value |
|---|---|---|
| Silica Gel 60 F$_{254}$ (E. Merck) | n-butanol:acetic acid:water (4:1:2) | 0.41 |

Infrared Spectrum
  $\nu_{max}^{KBr}$: 3350, 2930, 2850, 1650, 1640, 1520, 1460, 1270, 1250, 1050 (cm$^{-1}$)

¹H-NMR (500 MHz, CD₃OD, δ): 7.17 (1H, d, J=2 Hz), 6.89 (1H, dd, J=8 and 2 Hz), 6.81 (1H, d, J=8 Hz), 5.27 (1H, d, J=3 Hz), 5.08 (1H, d, J=4 Hz), 4.92 (1H, m), 4.63 (1H, dd, J=11 and 7 Hz), 4.57 (1H, m), 4.49 (1H, br s), 4.43 (1H, m), 4.41–4.36 (3H, m), 4.23 (1H, dd, J=12 and 4 Hz), 4.18 (1H, m), 4.09 (1H, m), 3.97 (1H, dd, J=11 and 3 Hz), 3.91 (1H, m), 3.78 (1H, br d, J=11 Hz), 3.74 (1H, br d, J=12 Hz), 3.36 (1H, m), 2.62 (1H, dd, J=16 and 4.5 Hz), 2.59 (2H, m), d, J=7 Hz), 2.53 (1H, m), 2.47 (1H, m), 2.43 (1H, dd, J=16 and 9 Hz), 2.21 (2H, m), 2.07–1.99 (2H, m), 1.94 (1H, m), 1.58 (2H, m), 1.34–1.23 (24H, m), 1.07 (3H, d, J=7 Hz), 0.89 (3H, t, J=7 Hz)

¹³C-NMR (125 MHz, D₂O, δ): 176.7 (s), 176.2 (s), 174.2 (s), 173.8 (s), 172.6 (s), 172.4 (s), 172.0 (s), 169.5 (s), 149.1 (s), 141.1 (s), 131.0 (s), 128.0 (d), 125.3 (d), 118.2 (d), 75.6 (d), 74.3 (d), 73.8 (d), 71.3 (d), 70.7 (d), 70.6 (d), 70.1 (d), 63.6 (t), 62.4 (d), 58.4 (d), 57.0 (t), 56.0 (d), 55.4 (d), 52.9 (t), 51.3 (d), 40.8 (t), 39.6 (t), 39.1 (d), 39.0 (t), 36.7 (t), 35.5 (t), 33.1 (t), 30.8 (t)×5, 30.7 (t), 30.6 (t), 30.5 (t), 30.4 (t), 30.3 (t), 26.9 (t), 23.7 (t), 14.4 (q), 11.1 (q)

From the analysis of the above physical and chemical properties, and the result of the further investigation of identification of chemical structure, the chemical structure of the WF 738A has been identified and assigned as follows.

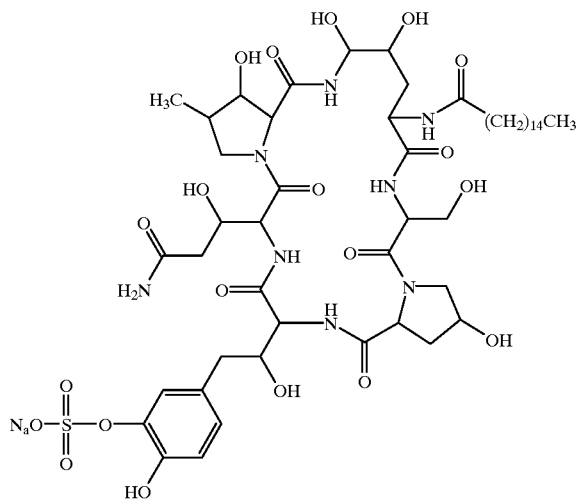

The WF 738C as obtained has the following physico-chemical properties.

HPLC Condition
  Column: YMC Pack ODS-AM303 (250 mm L.×4.6 mm I.D.; YMC Co., Ltd.)
  Eluent: 55% acetonitrile–0.5% NaH₂PO₄.2H₂O
  Flow rate: 1 ml/min
  Detection: UV at 210 nm
  Retention time: 9.0 minutes
Appearance
  white powder
Nature
  acid substance
Molecular Formula
  $C_{50}H_{79}N_8O_{19}SNa$ [free acid: $C_{50}H_{80}N_8O_{19}S$]
Molecular Weight
  Molecular weight: 1128 (free acid)
  ESI-MS: (m/z) 1129 (M+H)⁺
Melting Point
  155–160° C. (dec.)
Specific Rotation
  $[\alpha]_D$ 23 −2° (C 0.35, methanol)

Ultraviolet Absorption Spectrum
  $\lambda_{max}$ methanol: 277 nm (ε 1579)
Solubility
  Soluble: water, methanol, dimethylsulfoxide
  Insoluble: chloroform
Color Reaction
  Positive: iodine vapor reaction, ceric sulfate reaction
  Negative: ninhydrin reaction, Molish reaction, Dragendorff reaction, ferric chloride reaction
Thin Layer Chromatography (TLC)

| Stationary phase | Developing solvent | Rf value |
|---|---|---|
| Silica Gel 60 F₂₅₄ (E. Merck) | n-butanol:acetic acid:water (4:1:2) | 0.43 |

Infrared Spectrum
  $\nu_{max}$ KBr: 3350, 2920, 2850, 1650, 1640, 1540, 1520, 1450, 1270, 1050 (cm⁻¹)

¹H-NMR (500 MHz, CD₃OD, δ): 7.17 (1H, d, J=2 Hz), 6.89 (1H, dd, J=8 and 2 Hz), 6.80 (1H, d, J=8 Hz), 5.38 (1H, dd, J=10.5 and 3.5 Hz), 5.10 (1H, d, J=4 Hz), 4.94 (1H, br d, J=4 Hz), 4.60 (1H, dd, J=11 and 7 Hz), 4.57 (1H, m), 4.54 (1H, d, J=2 Hz), 4.42 (1H, m), 4.39–4.30 (3H, m), 4.26 (1H, dd, J=12 and 4 Hz), 4.13–4.07 (2H, m), 3.97 (1H, dd, J=11 and 4 Hz), 3.77–3.71 (2H, m), 3.35 (1H, m), 2.65 (1H, dd, J=16 and 4 Hz), 2.62–2.52 (3H, m), 2.46 (1H, m), 2.42 (1H, dd, J=16 and 9 Hz), 2.25 (2H, m), 2.08–1.96 (3H, m), 1.74–1.64 (2H, m), 1.59 (2H, m), 1.34–1.24 (24H, m), 1.07 (3H, d, J=7 Hz), 0.89 (3H, t, J=7 Hz)

¹³C-NMR (125 MHz, CD₃OD, δ): 176.9 (s), 176.3 (s), 174.5 (s), 174.1 (s), 172.8 (s), 172.5 (s), 171.8 (s), 169.1 (s), 149.1 (s), 141.1 (s), 131.1 (s), 128.0 (d), 125.3 (d), 118.2 (d), 76.0 (d), 73.9 (d), 71.9 (d), 71.3 (d), 70.6 (d), 70.3 (d), 63.8 (t), 62.5 (d), 58.2 (d), 57.0 (t), 56.0 (d), 55.4 (d), 52.9 (t), 52.0 (d), 40.8 (t), 39.5 (t), 39.1 (d), 39.0 (t), 36.8 (t), 33.1 (t), 30.9 (t), 30.8 (t)×5, 30.7 (t), 30.6 (t), 30.5 (t), 30.4 (t), 30.3 (t), 27.3 (t), 27.0 (t), 23.7 (t), 14.4 (q), 11.1 (q)

From the analysis of the above physical and chemical properties, and the result of the further investigation of identification of chemical structure, the chemical structure of the WF 738C has been identified and assigned as follows.

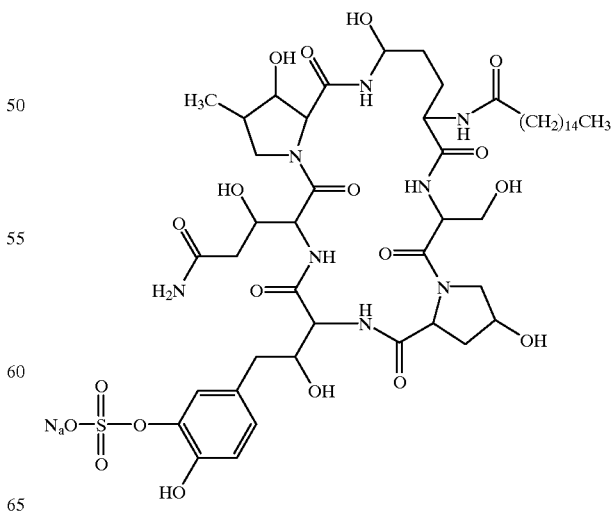

EXAMPLE 2

(1) Fermentation

The fermentation of Example 2 was carried out according to a similar manner to that of Example 1.

(2) Isolation and Purification

After the culture was completed, an equal volume of acetone was added to the cultured broth (20 l). The mixture was allowed to stand for about an hour with stirring at room temperature. The resultant mixture was filtered with an aid of diatomaceous earth, yielding about 30 l of the filtrate. The filtrate was diluted with an equal volume of water and passed through a column (1 l ) of Diaion HP-20 (Mitsubishi Chemical Co., Ltd.) packed with water. The column was washed with water (3 l) and 50% aqueous methanol (3 l) and then eluted with 80% aqueous methanol (3 l). The eluate was diluted with an equal volume of water. and applied onto a column (1 l) of YMC GEL (ODS-AM 120-S50, YMC Co., Ltd.) packed with water, and the col was eluted with 45% aqueous acetonitrile containing 0.5% $NaH_2PO_4.2H_2O$. Fractions containing the WF 738B were combined and concentrated in vacuo. The WF 738B was further purified by preparative HPLC, using a YMC-packed column (ODS-AM SH-343 5AM S-5, YMC Co., Ltd., 250 mm L.×20 mm I.D.) with 40% aqueous acetonitrile containing 0.3% $NaH_2PO_4.2H_2O$ as a mobile phase and flow rate of 9.9 ml/min.

Fractions containing the WF 738B were collected and concentrated in vacuo to give residual water. This residue was passed through a column (10 ml) of Diaion HP-20 packed with water. The column was washed with water (100 ml) and eluted with 80% aqueous methanol (30 ml). The eluate was concentrated in vacuo and lyophilized to give a white powder.

The powder was dissolved in methanol and preabsorbed on a small amount of silica gel and applied onto a silica gel column (20 ml) prepared with acetone. The column was eluted stepwise with acetone-methanol (10:1, 5:1, 3:1 and 1:1 v/v). The eluate from acetone-methanol (3:1 v/v) was concentrated in vacuo to give a white powder. The powder was dissolved in water and applied onto a column (1 ml) of Diaion HP-20 packed with water. The column was washed with water (5 ml) and eluted with 80% aqueous methanol (3 ml). The eluate was concentrated in vacuo and lyophilized to give 2.4 mg of the WF 738B as a white powder.

The WF 738B as obtained has the following physico-chemical properties.

HPLC Condition
  Column: YMC Pack ODS-AM AM303, S-5 120A (250 mm L.×4.6 mm I.D.; YMC Co., Ltd.)
  Eluent: 50% acetonitrile—0.5% $NaH_2PO_4.2H_2O$
  Flow rate: 1 ml/min
  Detection: UV at 210 nm
  Retention time: 10.3 minutes
Appearance
  white powder
Molecular Formula
  $C_{49}H_{77}N_8O_{20}SNa$ [free acid: $C_{49}H_{78}N_8O_{20}S$]
Molecular Weight
  Molecular weight: 1130 (free acid)
  ESI-MS (negative): (m/z) 1129 (M–H)⁻
  ESI-MS (positive): (m/z) 1131 (M+H)⁺
Melting Point
  160–164° C. (dec.)
Specific Rotation
  $[\alpha]_D$ 23–7.6° (C 0.5, methanol)
Ultraviolet Absorption Spectrum
  $\lambda_{max}$ water: 275 nm ($\epsilon$ 1900)
Solubility
  Soluble: water, methanol
  Insoluble: n-hexane
Color Reaction
  Positive: iodine vapor reaction, ceric sulfate reaction, ninhydrin reaction
  Negative: Molish reaction, ferric chloride reaction
Thin Layer Chromatography (TLC)

| Stationary phase | Developing solvent | Rf value |
|---|---|---|
| Silica Gel 60 $F_{254}$ (E. Merck) | n-butanol:acetic acid:water (4:1:2) | 0.45 |

Infrared Spectrum
  $\nu_{max}$ KBr: 3360, 2930, 2850, 1650 1630, 1540, 1520, 1440, 1280, 1250, 1050 $(cm^{-1})$
  $^1$H-NMR (500 MHz, $D_2O$, δ): 7.17 (1H, d, J=2 Hz), 6.89 (1H, dd, J=8 and 2 Hz), 6.80 (1H, d, J=8 Hz), 5.28 (1H, d, J=3 Hz), 5.11 (1H, d, J=4 Hz), 4.92 (1H, m), 4.63 (1H, m), 4.57 (1H, m), 4.49 (1H, m), 4.46–4.35 (4H, m), 4.30 (1H, m), 4.23 (1H, m), 4.01–3.89 (3H, m), 3.83–3.72 (3H, m), 2.64–2.57 (3H, m) 2.48–2.38 (2H, m), 2.31–2.19 (3H, m), 2.09–1.88 (4H, m), 1.58 (2H, m), 1.34–1.23 (24H, m), 0.89 (3H, t, J=7 Hz)
  $^{13}$C-NMR (125 MHz, $CD_3OD$, δ): 176.7 (s), 176.2 (s), 174.2 (s), 173.8 (s), 172.7 (s), 172.6 (s), 172.0 (s), 169.5 (s), 149.1 (s), 141.1 (s), 131.0 (s), 128.0 (d), 125.3 (d), 118.2 (d), 74.2 (d), 73.9 (d), 73.8 (d), 71.3 (d), 70.7 (d), 70.6 (d), 69.7 (d), 63.6 (t), 62.4 (d), 58.3 (d), 57.0 (t), 56.0 (d), 55.4 (d), 51.2 (d), 46.9 (t), 40.8 (t), 39.5 (t), 39.0 (t), 36.8 (t), 35.5 (t), 34.6 (t), 33.1 (t), 30.8 (t) ×5, 30.7 (t), 30.6 (t), 30.5 (t), 30.4 (t), 30.3 (t), 26.9 (t), 23.7 (t), 14.4 (q)

From the analysis of the above physical and chemical properties, and the result of the further investigation of identification of chemical structure, the chemical structure of the WF 738B has been identified and assigned as follows.

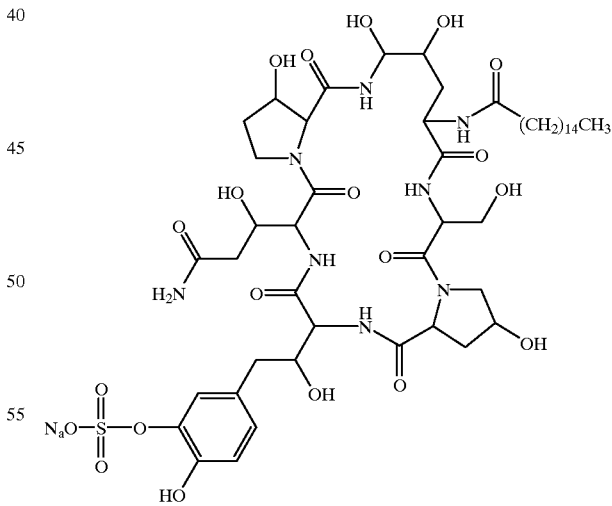

EXAMPLE 3

(1) Fermentation

The fermentation of Example 3 was carried out according to a similar manner to that of Example 1.

(2) Isolation and Purification

After the culture was completed, an equal volume of acetone was added to the cultured broth (20 l). The mixture was allowed to stand for about an hour with stirring at room temperature. The resultant mixture was filtered with an aid of diatomaceous earth, yielding about 30 l of the filtrate. The filtrate was diluted with an equal volume of water and passed through a column (1 l) of Diaion HP-20 (Mitsubishi Chemical Co., Ltd.) packed with water. The column was washed with water (3 l) and 50% aqueous methanol (3 l) and then eluted with 80% aqueous methanol (3 l). The eluate was diluted with an equal volume of water and applied onto a column (1 l) of YMC GEL (ODS-AM 120-S50, YMC Co., Ltd.) packed with water, and the column was eluted with 45% aqueous acetonitrile containing 0.5% $NaH_2PO_4.2H_2O$. Fractions containing the WF 738D2 were combined and concentrated in vacuo. The WF 738D2 was further purified by preparative HPLC, using a YMC-packed column (ODS-AM SH-343 5AM S-5, YMC Co., Ltd., 250 mm L.×20 mm I.D.) with 40% aqueous acetonitrile containing 0.3% $NaH_2PO_4.2H_2O$ as a mobile phase and flow rate of 9.9 ml/min.

Fractions containing the WF 738D2 were collected and concentrated in vacuo to give residual water. This residue was passed through a column (15 ml) of Diaion HP-20 packed with water. The column was washed with water (150 ml) and eluted with 80% aqueous methanol (50 ml). The eluate was concentrated in vacuo and lyophilized to give a white powder.

The powder was dissolved in methanol and preabsorbed on a small amount of silica gel and applied onto a column (10 ml) of silica gel 60 (230–400 mesH, Merck) prepared with acetone. The column was eluted with acetone-methanol (10:1 v/v). Fractions containing the FW 738D2 were combined and concentrated in vacuo. The WF 738D2 was further purified by preparative HPLC, using a YMC-packed column (ODS-AM SH-343 5AM S-5, YMC Co., Ltd., 250 mm L.×20 mm I.D.) with 50% aqueous acetonitrile containing 0.5% $NaH_2PO_4.2H_2O$ as a mobile phase and flow rate of 9.9 ml/min. Fractions containing the WF 738D2 were collected and concentrated in vacuo to give residual water. This residue was passed through a column (3 ml) of Diaion HP-20 packed with water. The column was washed with water (15 ml) and eluted with 80% aqueous methanol (12 ml). The eluate was added 1-butanol and concentrated in vacuo and lyophilized to give 2.8 mg of the WF 738D2 as a white powder.

The WF 738D2 as obtained has the following physicochemical properties.
HPLC Condition
  Column: YMC Pack ODS-AM303 (250 mm L.×4.6 mm I.D.; YMC Co., Ltd.)
  Eluent: 50% acetonitrile—0.5% $NaH_2PO_4.2H_2O$.
  Flow rate: 1 ml/min
  Detection: UV at 210 nm
  Retention time: 13.1 minutes
Appearance:
  white powder
Molecular Formula
  $C_{50}H_{79}N_8O_{18}SNa$ [free acid: $C_{50}H_{80}N_8O_{18}S$]
Molecular Weight
  Molecular weight: 1112 (free acid)
  ESI-MS (negative): (m/z) 1111 $(M-H)^-$
  ESI-MS (positive): (m/z) 1113 $(M+H)^+$
Specific Rotation
  $[\alpha]_D$ 23 –20° (C 0.25, methanol)
Ultraviolet Absorption Spectrum
  $\lambda_{max}$ water 278 nm ($\epsilon$ 2224)
Solubility
  Soluble water, methanol
  Insoluble: n-hexane
Color Reaction
  Positive: iodine vapor reaction, ceric sulfate reaction
  Negative: Molish reaction, ferric chloride reaction
Thin Layer Chromatography (TLC)

| Stationary phase | Developing solvent | Rf value |
|---|---|---|
| Silica Gel 60 $F_{254}$ (E. Merck) | n-butanol:acetic acid:water (4:1:2) | 0.50 |

Infrared Spectrum
  $\nu_{max}$ KBr: 3300, 2930, 2850, 1650, 1640, 1540, 1520, 1460, 1270, 1240, 1050 (cm$^{-1}$)
  $^1$H-NMR (500 MHz, CD$_3$OD, $\delta$) 7.12 (1H, d, J=2 Hz), 6.86 (1H, dd, J=8 and 2 Hz), 6.77 (1H, d, J=8 Hz), 5.35 (1H, dd, J=10 and 4 Hz), 5.07 (1H, d, J=4 Hz), 4.86 (1H, m), 4.51–4.45 (2H, m), 4.40–4.32 (3H, m), 4.31 (1H, d, J=2 Hz), 4.23 (1H, dd, J=11 and 4 Hz), 4.18–4.12 (2H, m), 3.81 (1H, d, J=11 Hz), 3.73 (1H, dd, J=11 and 3 Hz), 3.67 (1H, br d, J=11 Hz), 3.37 (1H, t, J=10 Hz), 2.66 (1H,. m), 2.59 (1H, dd, J=16 and 4 Hz), 2.56–2.47 (2H, m), 2.43 (1H, dd, J=16 and 9 Hz), 2.30–2.20 (4H, m), 2.05–1.90 (3H, m), 1.75–1.61 (3H, m), 1.59 (2H, m), 1.37–1.23 (24H, m), 1.06 (3H, d, J=7 Hz), 0.89 (3H, t, J=7 Hz)
  $^{13}$C-NMR (125 MHz, CD$_3$OD, $\delta$): 176.7 (s), 176.2 (s), 174.6 (s), 174.0 (s), 173.6 (s), 172.5 (s), 171.8 (s), 169.1 (s), 148.7 (s), 141.3 (s), 134.0 (s), 127.0 (d), 124.0 (d), 118.3 (d), 75.9 (d), 72.0 (d), 71.3 (d), 70.7 (d), 70.1 (d), 63.8 (t), 62.1 (d), 52.8 (t), 55.9 (d), 55.4 (d), 53.0 (t), 52.1 (d), 39.3 (t), 39.1 (d), 38.4 (t), 36.8 (t), 34.8 (t), 33.4 (t), 33.1 (t), 30.9 (t), 30.8 (t)×6, 30.7 (t), 30.6 (t), 30.5 (t), 30.4 (t), 27.4 (t), 27.0 (t), 23.8 (t), 14.5 (q), 11.2 (q)

From the analysis of the above physical and chemical properties, and the result of the further investigation of identification of chemical structure, the chemical structure of the WF 738D2 has been identified and assigned as follows.

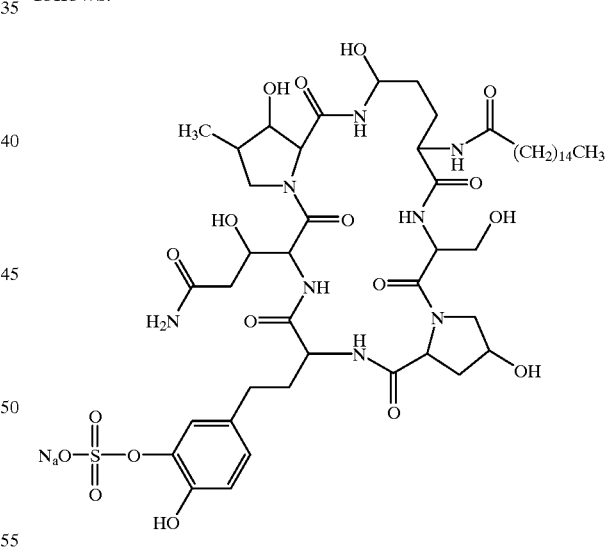

EXAMPLE 4

1) Fermentation of *Actinoplanes utahensis*

A stock culture of *Actinoplanes utahensis* IFO-13244 is prepared and maintained on agar slant. A loopful of the slant culture was inoculated into a seed medium consisting of starch 1%, sucrose 1%, glucose 1%, cotton seed flour 1%, peptone 0.5%, soy bean meal 0.5% and CaCO$_3$ 0.1%. The inoculated vegetative medium was incubated in a 225 ml-wide mouth Erlenmeyer flask at 30° C. for about 72 hours on a rotary shaker.

This incubated vegetative medium was used directly to inoculate into a production medium (20 l) consisting of sucrose 2%, peanut powder 1%, $K_2HPO_4$ 0.12%, $KH_2PO_4$ 0.05% and $MgSO_4 \cdot 7H_2O$ 0.025%. The inoculated production medium was allowed to ferment in a jar fermentor (30 l) at a temperature of 30° C. for about 80 hours. The fermentation medium was stirred with conventional agitators at 250 rpm and aerated at 20 l/min. The vegetative mycelium was collected from the fermented broth by filtration and once washed with water. The washed mycelium was directly used to obtain the Deacyl WF 738A.

(2) Reaction Condition

To a solution of the WF 738A (420 mg) in water (105 ml) was added 1M Na-phosphate buffer (pH 5.8) (15 ml) and a washed mycelium of Actinoplanes utahensis IFO-13244 (10 g wet weight). The reaction was carried out at 50° C. with stirring for 2 hours. The increase of the Deacyl WF 738A was monitored by HPLC indicated below.

From 420 mg of the WF 738A, 310 mg of the Deacyl WF 738A was formed in the reaction mixture.

HPLC Condition

Column: YMC Pack ODS-AM AM303, S-5 120A (250 mm L.×4.6 mm I.D.; YMC Co., Ltd.)
Eluent: 15% aqueous methanol—0.5% $NaH_2PO_4 \cdot 2H_2O$
Flow rate: 1 ml/min
Detection: UV at 210 nm
Retention time: 11.6 minutes (3) Isolation of the Deacyl WF 738A The reaction mixture described above was filtrated with filter aid. The mycelial cake was discarded. The filtrate hus obtained was passed through a column (70 ml) of SEPA-BEADS SP-207 (Mitsubishi Chemical Co., Ltd.) packed with water. The column was washed with water (210 ml) and then eluted with 50% aqueous methanol (210 ml). The eluate was concentrated in vacuo to an aqueous solution (75 ml) and added 375 mg of $NaH_2PO_4 \cdot 2H_2O$. The solution was passed through a column (100 ml) of YMC GEL ODS-AM 120-S50 (YMC Co., Ltd.) packed with water. The column was eluted with 4% aqueous acetonitrile containing 0.5% $NaH_2PO_4 \cdot 2H_2O$ and elution was monitored by HPLC indicated before. The portion corresponding to the Deacyl WF 738A was concentrated in vacuo to give residual water. This residue was further purified by preparative HPLC using a YMC-packed column (ODS-AM SH-343 5AM S-5, YMC Co., Ltd., 250 mm L.×20 mm I.D.) with 15% aqueous methanol containing 0.5% $NaH_2PO_4 \cdot 2H_2O$ as a mobile phase and flow rate of 9.9 ml/min. The portion corresponding to the Deacyl WF 738A was concentrated in vacuo to give residual water. This residue was passed through a column (50 ml) of DIAION HP-20 (Mitsubishi Chemical Co., Ltd.) packed with water. The column was washed with water (250 ml) and then eluted with 30% aqueous methanol. The eluate was concentrated in vacuo and lyophilized to give 82 mg of the Deacyl WF 738A as a white powder.

The Deacyl WF 738A as obtained has the following physico-chemical properties.

HPLC Condition

Column: YMC Pack ODS-AM AM303, S-5 120A (250 mm L.×4.6 mm I.D.; YMC Co., Ltd.)
Eluent: 15% methanol—0.5% $NaH_2PO_4 \cdot 2H_2O$
Flow rate: 1 ml/min
Detection: UV at 210 nm
Retention time: 11.6 minutes Appearance
  white powder Molecular Formula
  $C_{34}H_{49}N_8O_{19}SNa$ [free acid: $C_{34}H_{50}N_8O_{19}S$]

Molecular Weight
  Molecular weight: 906 (free acid)
  ESI-MS (negative): (m/z) 905 $(M-H)^-$
  ESI-MS (positive): (m/z) 907 $(M+H)^+$ Melting point
  163–168° C. (dec.)

Specific Rotation
  $[\alpha]_D$ 23 −16° (C 0.5, water)

Ultraviolet Absorption Spectrum
  $\lambda_{max}$ water: 277 nm (ϵ1900)

Solubility
  Soluble: water
  Slightly soluble: methanol
  Insoluble: ethyl acetate, n-hexane Color Reaction
  Positive: iodine vapor reaction, ceric sulfate reaction, ninhydrin reaction
  Negative: Molish reaction, ferric chloride reaction Thin Layer Chromatography (TLC)

| Stationary phase | Developing solvent | Rf value |
|---|---|---|
| Silica Gel 60 $F_{254}$ (E. Merck) | 70% aqueous isopropyl alcohol | 0.67 |

Infrared Spectrum
  $\nu_{max}$ KBR 3420, 2930, 1670, 1650, 1520, 1440, 1280, 1240, 1050 $(cm^{-1})$ $^1$H-NMR (500MHz, $D_2O$, δ) 7.20 (1H, d, J=2 Hz), 6.99 (1H, dd, J=8 and 2 Hz), 6.95 (1H, d, J=8 Hz), 5.38 (1H, d, J=3 Hz), 5.04 (1H, m), 4.92 (1H, d J=6 Hz), 4.71 (1H, m), 4.63 (1H, m), 4.48 (1H, m), 4.42–4.22 (5H, m), 4.12 (1H, m), 4.07–4.01 (2H, m), 3.93–3.87 (3H, m), 3.41 (1H, m), 2.78–2.68 (2H, m), 2.60–2.50 (2H, m), 2.45–2.34 (3H, m), 2.12 (1H, m), 2.02 (1H, m), 1.02 (3H, d, J=6 Hz)

$^{13}$C-NMR (125 MHz, $D_2O$, δ): 178.4 (s), 176.7 (s), 174.6 (s), 174.4 (s), 173.8 (s), 171.7 (s), 171.4 (s), 149.4 (s), 141.5 (s), 132.5 (s), 130.7 (d), 126.6 (d), 120.2 (d), 78.3 (d), 76.8 (d), 74.5 (d), 73.0 (d), 72.9 (d), 71.7 (d), 69.5 (d), 64.0 (t), 63.9 (d), 59.7 (d), 58.3 (t), 57.5 (d), 57.0 (d), 55.4 (d), 54.9 (t), 41.8 (t), 41.6 (t), 40.0 (t), 39.9 (d), 34.1 (t), 13.4 (q)

From the analysis of the above physical and chemical properties, and the result of the further investigation of identification of chemical structure, the chemical structure of the Deacyl WF 738A has been identified and assigned as follows.

EXAMPLE 5

(1) Fermentation of Actinoplanes Utahensis

The fermentation of Actinoplanes utahensis was carried out according to a similar manner to that of Example 4.

(2) Reaction Condition

To a solution of the WF 738B (5 g) in water (2.1 l) was added 1M Na-phosphate buffer (pH 5.8) (300 ml) and a washed mycelium of Actinoplanes utahensis IFO-13244 (300 g wet weight). The reaction was carried out at 50° C. with stirring for 1.5 hours. The increase of the Deacyl WF 738B was monitored by HPLC indicated below.

From 5 g of the WF 738B, 3.9 g of the Deacyl WF 738B was formed in the reaction mixture.

HPLC Condition
  Column: YMC Pack ODS-AM AM303, S-5 120A (250 mm L.×4.6 mm I.D.; YMC Co., Ltd.)
  Eluent: 15% aqueous methanol—0.5% $NaH_2PO_4.2H_2O$
  Flow rate: 1 ml/min
  Detection: UV at 210 nm
  Retention time: 7.2 minutes (3) Isolation of the Deacyl WF 738B The reaction mixture described above was filtrated with a filter aid. The mycelial cake was discarded. The filtrate thus obtained was passed through a column (800 ml) of SEPA-BEADS SP-207 (Mitsubishi Chemical Co., Ltd.) packed with water. The column was washed with water (2.4 l) and then eluted with 50% aqueous methanol (2 l). The eluate was concentrated in vacuo to an aqueous solution (620 ml) and added 3.1 g of $NaH_2PO_4.2H_2O$. The solution was passed through a column (2 l) of YMC GEL ODS-AM 120-S50 (YMC Co., Ltd) packed with water. The column was eluted with 2% aqueous acetonitrile containing 0.5% $NaH_2PO_4.2H_2O$ and elution was monitored by HPLC indicated before. The portion corresponding to the Deacyl WF 738B was concentrated in vacuo to give residual water. This residue was passed through a column (2 l) of YMC GEL ODS-AM 120-S50 (YMC Co., Ltd.) packed with water. The column was washed with water (10 l) and then eluted with 20% aqueous methanol. The eluate was concentrated in vacuo and lyophilized to give 1.15 g of the Deacyl WF 738B as a white powder.

The Deacyl WF 738B as obtained has the following physico-chemical properties.

HPLC Condition
  Column: YMC Pack ODS-AM AM303, S-5 120A (250 mm L.×4.6 mm I.D.; YMC Co., Ltd.)
  Eluent: 15% methanol—0.5% $NaH_2PO_4.2H_2O$
  Flow rate: 1 ml/min
  Detection: UV at 210 nm
  Retention time: 7.7 minutes Appearance
  white powder Molecular Formula
  $C_{33}H_{47}N_8O_{19}SNa$ [free acid: $C_{33}H_{48}N_8O_{19}S$]

Molecular Weight
  Molecular Weight: 892 (free acid)
  ESI-MS (negative): (m/z) 891 $(M-H)^-$
  ESI-MS (positive): (m/z) 893 $(M+H)^+$ Melting Point
  154–159° C. (dec.)

Specific Rotation
  $[\alpha]_D$ 23 −19° (C 0.75, water)

Ultraviolet Absorption Spectrum
  $\lambda_{max}$ water: 277 nm (ε 2187)

Solubility:
  Soluble: water
  Slightly soluble: methanol
  Insoluble: ethyl acetate, n-hexane Color Reaction:
  Positive: iodine vapor reaction, ceric sulfate reaction, ninhydrin reaction
  Negative: Molish reaction, ferric chloride reaction Thin Layer Chromatography (TLC)

| Stationary phase | Developing solvent | Rf value |
|---|---|---|
| Silica Gel 60 $F_{254}$ (E. Merck) | 70% aqueous isopropyl alcohol | 0.33 |

Infrared Spectrum $\lambda_{max}$ KBr: 3440, 2940, 1670, 1630, 1520, 1450, 1270, 1050 $(cm^{-1})$ $^1$H-NMR (500 MHz, $D_2O$, δ) 7.20 (1H, d, J=2 Hz), 6.97 (1H, dd, J=8 and 2 Hz), 6.95 (1H, d, J=8 Hz), 5.38 (1H, d, J=3.5 Hz), 5.06 (1H, m), 4.93 (1H, d J=6 Hz), 4.71 (1H, m), 4.62 (1H, m), 4.51–4.47 (2H, m), 4.43 (1H, d, J=2 Hz), 4.33 (1H, m), 4.27–4.22 (2H, m), 4.12 (1H, m), 4.08–4.02 (2H, m), 3.91–3.87 (2H, m), 3.82–3.78 (2H, m), 2.78–2.68 (2H, m), 2.54 (1H, m), 2.43–2.30 (4H, m), 2.16–1.97 (3H, m)

$^{13}$C-NMR (125 MHz, $D_2O$, δ) 178.4 (s), 176.8 (s), 174.6 (s), 174.4 (s), 173.8 (s), 171.7 (s), 171.2 (s), 149.5 (s), 141.5 (s), 132.5 (s), 130.7 (d), 126.5 (d), 120.2 (d), 78.2 (d), 75.2 (d), 74.6 (d), 72.9 (d), 72.8 (d), 71.8 (d), 70.2 (d), 64.0 (t), 63.9 (d), 59.7 (d), 58.4 (t), 57.5 (d), 57.0 (d), 55.4 (d), 48.6 (t), 41.7 (t), 41.6 (t), 39.9 (t), 35.4 (t), 34.1 (t)

From the analysis of the above physical and chemical properties, and the result of the further investigation of identification of chemical structure, the chemical structure of the Deacyl WF 738B has been identified and assigned as follows.

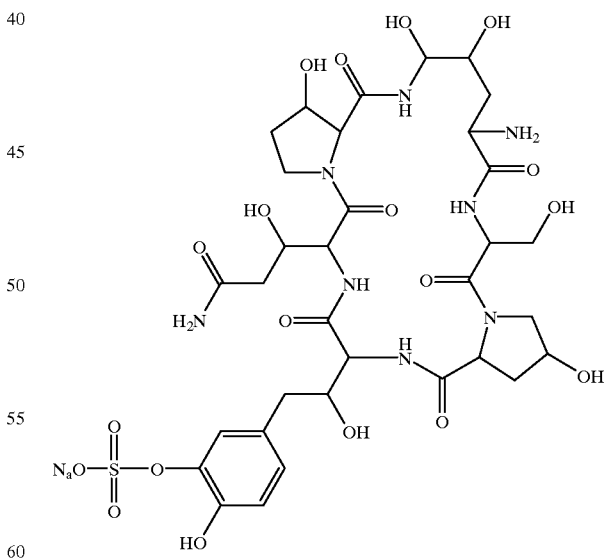

The Starting Compound in the following Example 6 to 17 and The Object Compounds (6) to (17) in the following Example 6 to 17 are illustrated by chemical formulae as below.

33
The Starting Compound (the same in Example 6 to 17)
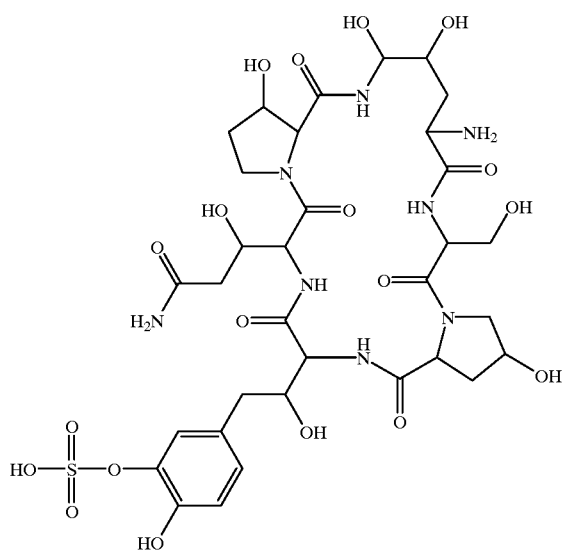
34
The Object Compounds (6) to (17)
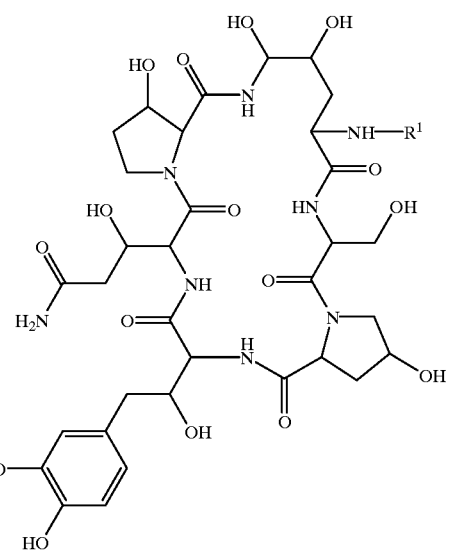
The Object Compound (X) [e.g. The Object Compound (6)] means the object compound of Example (X) [e.g. Example 6].
| The Object Compound | $R_1$ |
|---|---|
| 6 | 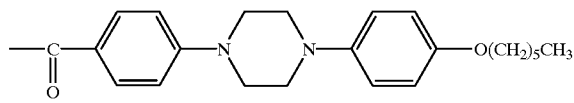 |
| 7 | 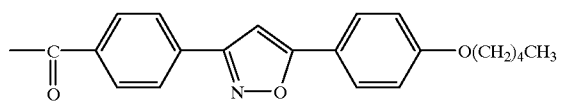 |
| 8 | 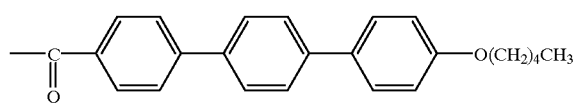 |
| 9 | 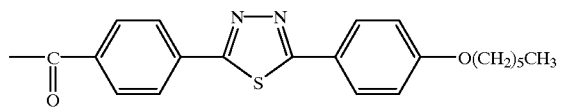 |
| 10 | 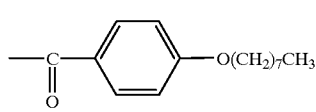 |
| 11 | 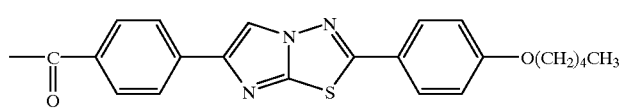 |
| 12 | 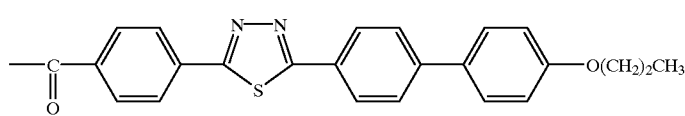 |

| The Object Compound | $R_1$ |
|---|---|
| 13 | 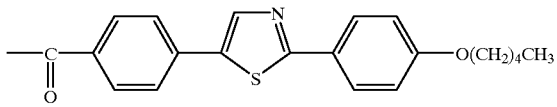 |
| 14 | 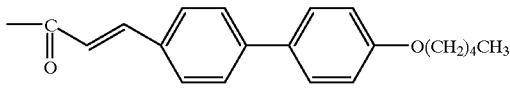 |
| 15 | 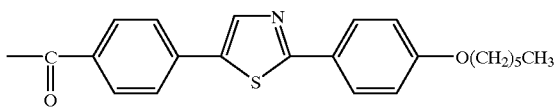 |
| 16 | 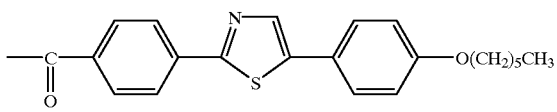 |
| 17 | 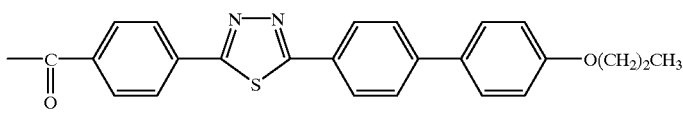 |

EXAMPLE 6

To a solution of The Starting Compound (0.1 g) and 1-[4-[4-(4-hexyloxyphenyl)piperazin-1-yl]benzoyloxy] benzotriazole (0.062 g) in dimethylformamide (2 ml) was added N,N-diisopropylethylamine (0.029 ml), and stirred for 5 hours at ambient temperature. The reaction mixture was pulverized with ethyl acetate. The precipitate was collected by filtration, and dried under reduced pressure. The powder was added to pH 6.86 phosphate buffer, and purified by preparative HPLC utilizing ODS resin which was eluted with a solvent system comprised of acetonitrile-pH 6.86 phosphate buffer (38:62) at a flow rate of 80 ml/minutes using a Shimadzu LC-8A pump. The column was monitored by a UV detector set at 210 nm. The fractions containing The Object Compound were combined, and evaporated under reduced pressure to remove acetonitrile. The residue was adjusted to pH 6.5 with saturated sodium bicarbonate aqueous solution, and subjected to column chromatography on ODS (YMC-gel ODS-AM.S-50) (Trademark: prepared by Yamamura Chemical Lab.), and washed with water, and eluted with 60% acetonitrile aqueous solution. The fractions containing The Object Compounds were combined, and evaporated under reduced pressure to remove acetonitrile. The residue was lyophilized to give The Object Compound (6) (105 mg).

IR (KBr): 3361.3, 1668.1, 1627.6, 1510.0, 1236.1, 1045.2 cm$^{-1}$

NMR (DMSO-d$_6$, δ): 0.88 (3H, t, J=6.6 Hz), 1.2–1.5 (6H, m), 1.6–2.6 (12H, m), 3.0–5.6 (35H, m), 6.6–7.15 (11H, m), 7.2–7.4 (2H, m), 7.56 (1H, d, J=9.7 Hz), 7.84 (2H, d, J=8.6 Hz), 8.19 (1H, d, J=9.2 Hz), 8.45 (1H, d, J=7.2 Hz), 8.69 (1H, d, J=7.2 Hz)

MASS (m/z): 1256 (M−Na)$^+$

Elemental Analysis Calcd. for $C_{56}H_{75}N_{10}NaO_{21}S.7H_2O$: C, 47.86; H, 6.38; N, 9.97.

Found: C, 47.81; H, 6.56; N, 10.46.

The following compounds [Example 7 to 17] were obtained according to a similar manner to that of Example 6.

EXAMPLE 7

The Object Compound (7)

IR (KBr): 3361, 1621.8, 1538.9, 1508.1, 1257.4, 1047.2 cm$^{-1}$

NMR (DMSO-d$_6$, δ): 0.91 (3H, t, J=7.0 Hz), 1.25–1.55 (4H, m), 1.65–2.60 (12H, m), 3.50–4.50 (15H, m), 4.06 (2H, d, J=6.5 Hz), 4.75 (8H, m), 5.42 (1H, m), 5.54 (1H, d, J=5.9 Hz), 6.70 (1H, d, J=8.2 Hz), 6.76 (1H, dd, J=8.2 and 1.5 Hz), 6.79 (1H, s), 6.96 (1H, d, J=1.5 Hz), 7.12 (2H, d, J=8.8 Hz), 7.23 (1H, s), 7.33 (1H, d, J=8.2 Hz), 7.45–7.65 (1H, m), 7.55 (1H, s), 7.85 (2H, d, J=8.8 Hz), 8.00 (2H, d, J=8.7 Hz), 8.06 (2H, d, J=8.7 Hz), 8.19 (1H, d, J=8.7 Hz), 8.69 (1H, d, J=7.0 Hz), 8.73 (1H, s), 8.87 (1H, d, J=7.3 Hz)

MASS (m/z): 1224.4 (M−Na)$^+$

Elemental Analysis Calcd. for $C_{54}H_{66}N_9NaO_{22}S.7H_2O$: C, 47.19; H, 5.87; N, 9.17.

Found C, 47.42; H, 5.62; N, 9.09.

EXAMPLE 8

The Object Compound (8)

IR (KBr): 3345.9, 1664.3, 1629.6, 1519.6, 1247.7, 1047.2 cm$^{-1}$

NMR (DMSO-d$_6$, δ): 0.91 (3H, t, J=7.0 Hz), 1.25–1.55 (4H, m), 1.65–2.65 (12H, m), 3.45–5.50 (27H, m), 6.70 (1H, d, J=8.2 Hz), 6.77 (1H, d, J=8.2 Hz), 6.86 (1H, s), 6.90–7.15 (2H, m), 7.04 (2H, d, J=8.7 Hz), 7.22 (1H, s), 7.50–7.95 (7H, m), 7.67 (2H, d, J=8.7 Hz), 8.01 (2H, d, J=8.5 Hz), 8.15–8.3 (1H, m), 8.5–9.0 (3H, m)

MASS (m/z): 1234 (M−Na)$^+$

Elemental Analysis Calcd. for $C_{57}H_{69}N_8NaO_{21}S.8H_2O$: C, 48.85; H, 6.11; N, 8.00.

Found: C, 48.78; H, 5.84; N, 7.92.

EXAMPLE 9

The Object Compound (9)

IR (KBr): 3340.1, 1629.6, 1515.8, 1444.4, 1257.4, 1047.2 cm$^{-1}$

NMR (DMSO-d$_6$, δ): 0.89 (3H, t, J=6.9 Hz), 1.2–1.55 (6H, m), 1.65–2.60 (12H, m), 3.50–4.55 (15H, m), 4.08 (2H, d, J=6.5 Hz), 4.7–5.3 (8H, m), 5.43 (1H, m), 5.54 (1H, d, J=5.9 Hz), 6.70 (1H, d, J=8.1 Hz), 6.76 (1H, d, J=8.1 Hz), 6.85 (1H, s), 6.96 (1H, s), 7.13 (2H, d, J=8.9 Hz), 7.21 (1H, s), 7.33 (1H, d, J=8.3 Hz), 7.55 (1H, d, J=8.9 Hz), 7.97 (2H, d, J=8.9 Hz), 8.07 (1H, d, J=9.5 Hz), 8.12 (1H, d, J=9.5 Hz), 8.20 (1H, d, J=9.0 Hz), 8.6–8.8 (1H, m), 8.73 (1H, s), 8.93 (1H, d, J=6.6 Hz)

MASS (m/z): 1256 (M–Na)$^+$

Elemental Analysis Calcd. for $C_{54}H_{67}N_{10}NaO_{21}S_2 \cdot 6H_2O$: C, 46.75; H, 5.73; N, 10.10.

Found: C, 46.57; H, 5.66; N, 10.03.

EXAMPLE 10

The Object Compound (10)

IR (KBr): 3340, 1666.2, 1629.6, 1508.1, 1255.4, 1045.2 cm$^{-1}$

NMR (DMSO-d$_6$, δ): 0.86 (3H, t, J=6.6 Hz), 1.2–1.55 (10H, m), 1.6–2.60 (12H, m), 3.50–4.55 (15H, m), 4.02 (2H, d, J=6.4 Hz), 4.7–5.3 (8H, m), 5.40 (1H, m), 5.48 (1H, d, J=5.9 Hz), 6.70 (1H, d, J=8.1 Hz), 6.76 (1H, d, J=8.1 Hz), 6.81 (1H, s), 6.95 (1H, s), 6.97 (2H, d, J=8.8 Hz), 7.28 (1H, s), 7.33 (1H, d, J=8.3 Hz), 7.55 (1H, d, J=8.4 Hz), 7.86 (2H, d, J=8.8 Hz), 8.18 (1H, d, J=9.3 Hz), 8.56 (1H, d, J=8.1 Hz), 8.6–8.8 (1H, m), 8.72 (1H, s)

MASS (m/z): 1124 (M–Na)$^+$

EXAMPLE 11

The Object Compound (11)

IR (KBr): 3340, 1666.2, 1629.6, 1519.6, 1047.2 cm$^{-1}$

NMR (DMSO-d$_6$, δ): 0.87 (3H, t, J=7.0 Hz), 1.2–1.5 (4H, m), 1.6–2.6 (12H, m), 3.50–4.55 (15H, m), 4.08 (2H, d, J=6.5 Hz), 4.7–5.3 (8H, m), 5.42 (1H, m), 5.53 (1H, d, J=5.9 Hz), 6.71 (1H, d, J=8.1 Hz), 6.76 (1H, d, J=8.1 Hz), 6.85 (1H, s), 6.96 (1H, s), 7.14 (2H, d, J=8.9 Hz), 7.27 (1H, s), 7.32 (1H, d, J=8.0 Hz), 7.56 (1H, d, J=8.7 Hz), 7.90 (2H, d, J=8.9 Hz), 7.98 (4H, s), 8.20 (1H, d, J=9.5 Hz), 8.6–8.8 (2H, m), 8.73 (1H, s), 8.86 (1H, s)

MASS (m/z): 1281 (M–Na)$^+$

Elemental Analysis Calcd. for $C_{55}H_{66}N_{11}NaO_{21}S_2 \cdot 7H_2O$: C, 46.18; H, 5.64; N, 10.77.

Found: C, 46.09; H, 5.72; N, 10.60.

EXAMPLE 12

The Object Compound (12)

IR (KBr): 3340, 1666.2, 1650.8, 1631.5, 1535.1, 1511.9, 1442.5, 1247.7 cm$^{-1}$

NMR (DMSO-d$_6$, δ): 1.00 (3H, t, J=7.4 Hz), 1.6–2.60 (12H, m), 3.50–4.55 (15H, m), 4.00 (2H, d, J=6.5 Hz), 4.7–5.3 (8H, m), 5.44 (1H, m), 5.55 (1H, d, J=5.9 Hz), 6.71 (1H, d, J=8.1 Hz), 6.76 (1H, d, J=8.1 Hz), 6.86 (1H, s), 6.96 (1H, s), 7.07 (2H, d, J=8.8 Hz), 7.22 (1H, s), 7.34 (1H, d, J=8.4 Hz), 7.56 (1H, d, J=8.6 Hz), 7.73 (2H, d, J=8.8 Hz), 7.86 (2H, d, J=8.4 Hz), 8.18 (1H, d, J=9.3 Hz), 8.05–8.3 (7H, m), 8.6–8.8 (1H, m), 8.73 (1H, s), 8.94 (1H, d, J=7.0 Hz)

MASS (m/z): 1289 (M–Na)$^{30}$

Elemental Analysis Calcd. for $C_{57}H_{65}N_{10}NaO_{21}S_2 \cdot 7H_2O$: C, 47.56; H, 5.53; N, 9.73.

Found: C, 47.86; H, 5.60; N, 9.70.

Example 13

The Object Compound (13)

IR (KBr): 3390.2, 2954.4, 2933.2, 1629.6, 1519.6, 1440.6, 1255.4, 1049.1 cm$^{-1}$

NMR (DMSO-d$_6$, δ) 1.80–1.00 (3H, m), 1.25–1.60 (4H, m), 1.60–1.70 (12H, m), 3.50–4.60 (17H, m), 4.78 (2H, d, J=6.1 Hz), 4.95 (2H, d, J=6.3 Hz), 5.05–5.35 (4H, m), 5.42 (1H, s), 5.54 (2H, d, J=5.8 Hz), 6.71 (2H, d, J=8.2 Hz), 6.77 (2H, d, J=8.2 Hz), 6.85 (1H, s), 6.96 (1H, s), 7.08 (2H, d, J=8.8 Hz), 7.24 (1H, s), 7.35 (2H, d, J=8.2 Hz), 7.58 (2H, d, J=8.4 Hz), 7.81 (2H, d, J=8.4 Hz), 7.92 (2H, d, J=8.8 Hz), 7.99 (2H, d, J=8.4 Hz), 8.21 (1H, d, J=8.7 Hz), 8.40 (1H, s), 8.69 (1H, d, J=7.0 Hz), 8.73 (1H, s), 8.83 (1H, d, J=7.3 Hz)

MASS (m/z): 1240.30 (M–Na)$^{30}$

Elemental Analysis Calcd. for $C_{54}H_{66}N_9NaO_{21}S_2 \cdot 6H_2O$: C, 47.26; H, 5.73; N, 9.19.

Found: C, 47.34; H, 5.58; N, 9.20.

EXAMPLE 14

The Object Compound (14)

IR (KBr): 3365, 1660.4, 1623.8, 1517.7, 1247.7, 1047.2 cm$^{-1}$

NMR (DMSO-d$_6$, δ): 0.91 (3H, t, J=7.1 Hz), 1.2–1.55 (4H, m), 1.6–2.60 (12H, m), 3.50–4.55 (15H, m), 4.01 (2H, d, J=6.4 Hz), 4.7–5.3 (8H, m), 5.39 (1H, m), 5.53 (1H, d, J=5.9 Hz), 6.70 (1H, d, J=8.1 Hz), 6.75 (1H, d, J=14 Hz), 6.76 (1H, d, J=8.1 Hz), 6.85 (1H, s), 6.95 (1H, s), 7.02 (2H, d, J=8.8 Hz), 7.30 (1H, s), 7.33 (1H, d, J=8.3 Hz), 7.40 (1H, d, J=14 Hz), 7.5–7.8 (7H, m), 8.23 (1H, d, J=8.7 Hz), 8.52 (1H, d, J=7.8 Hz), 8.6–8.8 (1H, m), 8.71 (1H, s)

MASS (m/z) 1184 (M–Na)$^{30}$

EXAMPLE 15

The Object Compound (15)

IR (KBr): 3390.2, 2954.4, 2933.2, 1629.6, 1519.6, 1440.6, 1255.4, 1049.1 cm$^{-1}$

NMR (DMSO-d$_6$, δ) 1.80–1.00 (3H, m), 1.20–1.55 (6H, m), 1.60–2.60 (12H, m), 3.50–4.60 (17H, m), 4.78 (2H, d, J=6.1 Hz), 4.95 (2H, d, J=6.3 Hz), 5.05–5.35 (4H, m), 5.42 (1H, s), 5.54 (2H, d, J=6.0 Hz), 6.71 (2H, d, J=8.3 Hz), 6.77 (2H, d, J=8.3 Hz), 6.85 (1H, s), 6.96 (1H, s), 7.08 (2H, d, J=8.8 Hz), 7.24 (1H, s), 7.33 (2H, d, J=8.3 Hz), 7.56 (2H, d, J=9.9 Hz), 7.81 (2H, d, J=8.4 Hz), 7.91 (2H, d, J=8.8 Hz), 7.99 (2H, d, J=8.4 Hz), 8.21 (1H, d, J=8.3 Hz), 8.40 (1H, s), 8.69 (1H, d, J=7.0 Hz), 8.73 (1H, s), 8.81 (1H, d, J=7.1 Hz)

MASS (m/z): 1253.55 (M–Na)$^{30}$

Elemental Analysis Calcd. for $C_{55}H_{68}N_9NaO_{21}S_2 \cdot 6H_2O$: C, 47.65; H, 5.82; N, 9.09.

Found: C, 47.67; H, 5.65; N, 9.06.

EXAMPLE 16

The Object Compound (16)

IR (KBr): 3425.0, 2933.2, 2861.8, 1633.4, 1533.1, 1444.4, 1251.6 cm$^{-1}$

NMR (DMSO-d$_6$δ): 1.80–1.00 (3H, m), 1.20–1.55 (6H, m), 1.60–2.60 (12H, m), 3.50–4.60 (17H, m), 4.78 (2H, d, J=6.0 Hz), 4.95 (2H, d, J=6.3 Hz), 5.05–5.35 (4H, m), 5.43 (1H, s), 5.55 (2H, d, J=5.9 Hz), 6.71 (2H, d, J=8.2 Hz), 6.77 (2H, d, J=8.2 Hz), 6.85 (1H, s), 6.96 (1H, s), 7.04 (2H, d, J=8.8 Hz), 7.23 (1H, s), 7.33 (2H, d, J=7.1 Hz), 7.56 (2H, d, J=8.2 Hz), 7.67 (2H, d, J=8.8 Hz), 8.04 (4H, s), 8.21 (1H, d, J=8.3 Hz), 8.27 (1H, s), 8.69 (1H, d, J=7.0 Hz), 8.73 (1H, s), 8.89 (1H, d, J=7.1 Hz)

MASS (m/z): 1254.07 (M–Na)$^{30}$

Elemental Analysis Calcd. for $C_{55}H_{68}N_9NaO_{21}S_2 \cdot 6H_2O$: C, 47.65; H, 5.82; N, 9.09.

Found: C, 47.46; H, 5.71; N, 9.07.

EXAMPLE 17

The Object Compound (17)

IR (KBr): 3467.4, 2964.1, 2939.0, 1629.6, 1517.7, 1440.6, 1247.7, 1047.2 cm$^{-1}$

NMR (DMSO-d$_6$, δ): 1.00 (3H, t, J=7.4 Hz), 1.60–2.70 (12H, m), 3.45–4.50 (17H, m), 4.50–5.40 (10H, m), 6.65–6.95 (3H, m), 6.96 (1H, s), 7.06 (2H, d, J=8.8 Hz), 7.23 (2H, br s), 7.56 (1H, m), 7.71 (2H, d, J=8.8 Hz), 7.75–7.95 (4H, m), 7.95–8.15 (4H, m), 8.20 (1H, m), 8.35–9.0 (4H, m)

MASS (m/z): 1288.14 (M−Na)$^{30}$

Elemental Analysis Calcd. for $C_{58}H_{66}N_9NaO_{21}S_2 \cdot 7H_2O$: C, 48.43; H, 5.61; N, 8.76.

Found: C, 48.69; H, 5.41; N, 8.67.

EXAMPLE 18

(1) Fermentation of Streptomyces sp. No. 6907

A stock culture of Streptomyces sp. No. 6907 is prepared and maintained on agar slant. A loopful of the slant culture was inoculated into 60 ml of sterilized seed medium consisting of maltose 3%, dried yeast 1%, CaCO$_3$ 0.5% in a 225-ml Erlenmeyer flask. The flask was incubated at 30° C. for 3 days on a rotary shaker (220 rpm, 5.1 cm-throw) and then inoculated (0.1%) into 160 ml of sterilized seed medium consisting of maltose 3%, dried yeast 1%, CaCO$_3$ 0.5%, Adekanol LG-109 (Asahi Denka Co., Ltd.) 0.1% and Silicone KM-70 (Shin-Etsu chemical Co., Ltd.) 0.1% in each of seven 500-ml Erlenmeyer flasks. And the flasks were incubated at 30° C. for 2 days on a rotary shaker (220 rpm, 5.1 cm-throw).

The resultant seed culture was then inoculated (5%) into 20 liters of sterilized production medium consisting of maltose 8%, soybean meal 2%, wheat germ 2%, potato protein 2%, CaCO$_3$ 0.5%, Adekanol LG-109 0.1% and Silicone KM-70 0.1% in a 30-liter-jar fermenter. The fermentation was carried out at 30° C. for 5 days under aeration of 20 liters/minute and agitation of 200 rpm. The fermentation broth was directly used to obtain the Deacyl WF 738C.

(2) Fermentation of *Coleophoma Crateriformis* No. 738

The formentaion of Example 18 was carried out according to a similar manner to that of Example 1.

(3) Preparation of the Crude WF 738 C

After the above culture was completed, an equal volume of acetone was added to the cultured broth (120 liters). The mixture was allowed to stand for about an hour with stirring at room temperature. The resultant mixture was filtrated with an aid of diatomaceous earth. The filtrate was diluted with an equal volume of water and passed through a column (12 liters) of DIAION HP-20 (Mitsubishi Chemical Co., Ltd.) packed with water. The column was washed with water (40 liters) and 50% aqueous methanol (40 liters) and then eluted with 90% aqueous methanol (24 liters). The eluate was concentrated in vacuo to an aqueous solution (1300 ml).

(4) Reaction Condition 300 ml of 1M Na-phosphate buffer (pH5.8) and 700 ml of the fermentation broth of Streptomyces sp. No. 6907 were added to the solution obtained above. This reaction mixture was adjusted to 6 liters with water. The reaction was carried out at 50° C. with stirring for an hour. The increase of the Deacyl WF 738C was monitored by analytical HPLC indicated below.

Analytical HPLC Condition

Column: TSKgel Amide-80 (250×4.6 mm I.D., TOSOH Co., Ltd.)

Eluent: 70% aqueous acetonitrile containing 0.05% Trifluoroacetic acid

Flow rate: 1 ml/min.

Detection: UV at 210 nm

Retention time: 9.2 minutes (5) Isolation of the Deacyl WF 738C

The reaction mixture described above was filtrated with an aid of diatomaceous earth. The mycelial cake was discarded. The filtrate thus obtained was passed through a column (3.2 liters) of SEPABEADS SP-207 (Mitsubishi Chemical Co., Ltd.) packed with water. The column was washed with water (9.5 liters) and then eluted with 50% aqueous methanol (7 liters). The eluate was concentrated in vacuo to an aqueous solution (1300 ml). This solution was passed through a column (8 liters) of YMC GEL (ODS-AM 120-S50, YMC Co., Ltd.) packed with water. The column was washed with 4% aqueous acetonitrile containing 0.5% NaH$_2$PO$_4 \cdot$2H$_2$O (63 liters) and eluted with 8% aqueous acetonitrile containing 0.5% NaH$_2$PO$_4 \cdot$2H$_2$O. Elution was monitored by analytical HPLC indicated before. Fractions containing the Deacyl WF 738C was concentrated in vacuo to give residual water. This residue was passed through a column (300 ml) of YMC GEL (ODS-AM 120-S50) packed with water. The column was washed with water (1500 ml) and then eluted with 20% aqueous methanol. The eluate was concentrated in vacuo and lyophilized to give 2 g of the Deacyl WF 738C as a pale yellowish powder. This powder was dissolved in a small volume of water and passed through a column (2 liters) of YMC GEL (ODS-AM 120-S50) packed with water. The column was eluted with 10% aqueous methanol. Fractions containing the Deacyl WF 738C was concentrated in vacuo and further purified by preparative HPLC, using TSKgel Amide-80 column (300×21.5 mm I.D., TOSOH Co., Ltd.) with 75% aqueous acetonitrile containing 10 mM NaH$_2$PO$_4 \cdot$2H$_2$O as a mobile phase and a flow rate of 5.6 ml/minute. Fractions containing the Deacyl WF 738C were collected and concentrated in vacuo to give residual water. This residue was passed through YMC-packed column (ODS-AM SH-343-5AM S-5, 250×20 mm I.D., YMC Co., Ltd.) equilibrated with water. The column was washed with water (400 ml) and then eluted with 20% aqueous methanol at a flow rate of 9.9 ml/minute. The eluate was concentrated in vacuo and lyophilized to give 42.2 mg of the Deacyl WF 738C as a white powder.

The Deacyl WF 738C as obtained has the following physico-chemical properties.

HPLC Condition

Column: YMC Pack ODS-AM AM303, S-5 120A (250 mm L.×4.6 mm I.D.; YMC Co., Ltd.)

Eluent: 15% methanol—0.5% NaH$_2$PO$_4 \cdot$2H$_2$O

Flow rate: 1 ml/min

Detection: WV at 210 nm

Retention time: 10.2 minutes

Appearance white powder

Molecular Formula $C_{34}H_{50}N_8O_{18}S$

Molecular Weight

Molecular weight: 890.88

ESI-MS (negative): (m/z) 889 (M−H)$^-$

ESI-MS (positive): (mlz) 891 (M+H)$^+$

Melting Point

215–223° C. (dec.)

Specific Rotation

[α]$_D$ 23−16°(C 1.0, water)

Ultraviolet Absorption Spectrum

λ$_{max}$ water: 276 nm (ε 1200)

Solubility

Soluble: water

Slightly soluble: methanol

Insoluble: ethyl acetate, n-hexane

Color Reaction

Positive: iodine vapor reaction, ceric sulfate reaction

Negative: Molish reaction, ferric chloride reaction

Thin Layer Chromatography (TLC)

| Stationary phase | Developing solvent | Rf value |
|---|---|---|
| Silica Gel 60 $F_{254}$ (E. Merck) | 70% aqueous isopropyl alcohol | 0.67 |

Infrared Spectrum $v_{max}$ KBr: 3370, 2950, 1670, 1630, 1520, 1450, 1270, 1240, 1050 (cm$^{-1}$)

$^1$H-NMR (500 MHz, D$_2$O, δ): 7.20 (1H, d, J=2 Hz), 6.98 (1H, dd, J=8 and 2 Hz), 6.96 (1H, d, J=8 Hz), 5.56 (1H, m), 5.07 (1H, m), 4.99 (1H, d, J=6 Hz), 4.71 (1H, m), 4.62 (1H, m), 4.50–4.43 (2H, m), 4.35 (1H, m), 4.33–4.26 (3H, m), 4.07(1H, m), 3.97 (1H, m), 3.93–3.82 (3H, m), 3.47 (1H, m), 2.75–2.65 (2H, m), 2.62–2.47 (3H, m), 2.36 (1H, m), 2.24–2.10 (2H, m), 2.04–1.90 (3H, m), 1.04 (3H, d, J=7 Hz)

$^{13}$C-NMR (125 MHz, D$_2$O, δ): 178.5 (s), 176.7 (s), 174.7 (s), 174.7 (s), 173.3 (s), 172.0 (s), 170.9 (s), 149.4 (s), 141.5 (s), 132.5 (s), 130.7 (d), 126.5 (d), 120.2 (d), 77.3 (d), 75.0 (d), 73.5 (d), 73.0 (d), 71.8 (d), 70.0 (d), 64.5 (t), 63.9 (d), 59.5 (d), 58.3 (t), 57.5 (d), 56.9 (d), 54.9 (t), 54.3 (d), 41.6 (t), 41.5 (t), 40.0 (d), 39.9 (t), 31.6 (t), 29.1 (t), 13.3 (q)

From the analysis of the above physical and chemical properties, and the result of the further investigation of identification of chemical structure, the chemical structure of the Deacyl WF 738C has been identified and assigned as follows.

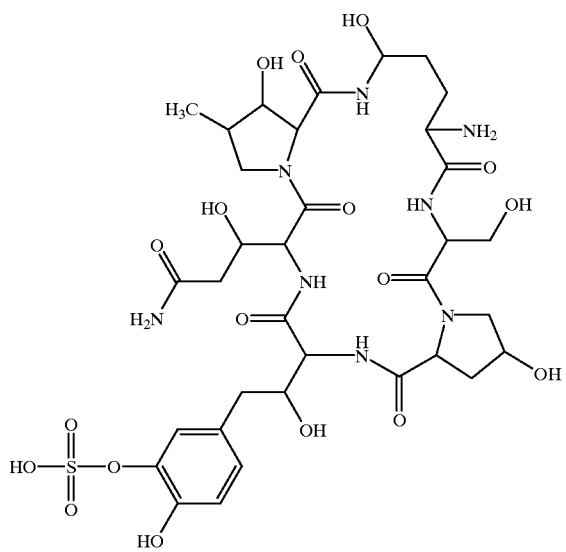

EXAMPLE 19

(1) Fermentation of Streptomyces sp. No. 6907

The fermentation of Streptomyces sp. No. 6907 of Example 19 was carried out according to a similar manner to that of Example 18.

(2) Fermentation of Coleophoma Crateriformis No. 738

The fermentation of Example 19 was carried out according to a similar manner to that of Example 1.

(3) Preparation of the Crude Deacyl WF 738F

After the above culture was completed, an equal volume of acetone was added to the cultured broth (180 liters). The mixture was allowed to stand for about an hour with stirring at room temperature. The resultant mixture was filtrated with an aid of diatomaceous earth. The filtrate was diluted with an equal volume of water and passed through a column (18 liters) of DIAION HP-20 (Mitsubishi Chemical Co., Ltd.) packed with water. The column was washed with water (60 liters) and 50% aqueous methanol (60 liters) and then eluted with 90% aqueous methanol (38 liters). The eluate was concentrated in vacuo to an aqueous solution (2 liters).

450 ml of 1M Na-phosphate buffer (pH5.8) and 1 liter of the fermentation broth of Streptomyces sp. No. 6907 were added to this solution (2 liters). This reaction mixture was adjusted to 9 liters with water. The reaction was carried out at 50° C. with stirring for an hour.

(4) Isolation of the Deacyl WF 738F

The reaction mixture described above was filtrated with an aid of diatomaceous earth. The mycelial cake was discarded. The filtrate thus obtained was passed through a column (5 liters) of SEPABEADS SP-207 (Mitsubishi Chemical Co., Ltd.) packed with water. The column was washed with water (15 liters) and then eluted with 50% aqueous methanol (12 liters). The eluate was concentrated in vacuo to an aqueous solution (2 liters). This solution was passed through a column (12 liters) of YMC GEL (ODS-AM 120-S50, YMC Co., Ltd.) packed with water. The column was eluted with 4% aqueous acetonitrile containing 0.5% NaH$_2$PO$_4$.2H$_2$O. Elution was monitored by analytical HPLC indicated below. Fractions containing the Deacyl WF 738F was concentrated in vacuo to give residual water. This residue was passed through a column (4 liters) of YMC GEL (ODS-AM 120-S50) packed with water. The column was eluted with 6.5% aqueous methanol. Fractions containing the Deacyl WF 738F was concentrated in vacuo and passed through a column (350 ml) of YMC GEL (ODS-AM 120-S50) packed with water. The column was eluted with 7% aqueous methanol. Fractions containing the Deacyl WF 738F was concentrated in vacuo and lyophilized to give a white powder (96.6 mg). This powder was dissolved in 400 ml of water and allowed to stand at room temperature to give 28.9 mg of the Deacyl WF 738F substance as colorless prisms.

Analytical HPLC Condition

Column: TSKgel Amide-80 (250×4.6 mm I.D., TOSOH Co., Ltd.)

Eluent: 70% aqueous acetonitrile containing 0.05% Trifluoroacetic acid

Flow rate: 1 ml/min.

Detection: UV at 210 nm

Retention time: 10.6 minutes

The Deacyl WF 738F as obtained has the following physico-chemical properties.

HPLC Condition

Column: YMC Pack ODS-AM AM303, S-5 120A (250 mm L.×4.6 mm I.D.; YMC Co., Ltd.)

Eluent: 15% methanol—0.5% NaH$_2$PO$_4$2H$_2$O

Flow rate: 1 ml/min

Detection: UV at 210 nm

Retention time: 6.9 minutes

Appearance

Colorless prisms

Molecular Formula $C_{33}H_{48}N_8O_{18}S$

Molecular Weight

Molecular weight: 876.85

ESI-MS (negative): (m/z) 875 (M−H)$^-$

ESI-MS (positive): (m/z) 877 (M+H)$^+$

Melting Point

200–212° C. (dec.)

Specific Rotation $[α]_D$ 23–19° (C 0.7, water)

Ultraviolet Absorption Spectrum $λ_{max}$ water: 277.5 nm (ε 1800)

Solubility

Soluble: water

Slightly soluble: methanol

Insoluble: ethyl acetate, n-hexane

Color Reaction

Positive: iodine vapor reaction, ceric sulfate reaction

Negative: Molish reaction, ferric chloride reaction

Thin Layer Chromatography (TLC)

| Stationary phase | Developing solvent | Rf value |
|---|---|---|
| Silica Gel 60 $F_{254}$ (E. Merck) | 70% aqueous isopropyl alcohol | 0.64 |

Infrared Spectrum $v_{max}$ KBr: 3360, 2950, 1670, 1630, 1540, 1515, 1450, 1270, 1240, 1040 (cm$^{-1}$)

$^1$H-NMR (500 MHz, D$_2$O, δ): 7.20 (1H, d, J=2 Hz), 6.99 (1H, dd, J=8 and 2 Hz), 6.96 (1H, d, J=8 Hz), 5.56 (1H, m), 507 (1H, m), 5.00 (1H, d, J=6 Hz), 4.72 (1H, m), 4.62 (1H, m), 4.49–4.43 (3H, m), 4.31–4.27 (2H, m), 4.16 (1H, d, J=5 Hz), 4.07 (1H, m), 3.94–3.80 (5H, m), 2.75–2.65 (2H, m), 2.54 (1H, m), 2.48 (1H, m), 2.40–2.32 (2H, m), 2.20 (1H, m), 2.14 (1H, m), 2.10–1.90 (4H, m)

$^{13}$C-NMR (125 MHz, D$_2$O, δ): 178.5 (s), 176.7 (s), 174.9 (s), 174.7 (s), 173.4 (s), 172.0 (s), 170.8 (s), 149.4 (s), 141.5 (s), 132.5 (s), 130.7 (d), 126.5 (d), 120.2 (d), 75.7 (d), 75.0 (d), 73.5 (d), 73.0 (d), 71.9 (d), 70.5 (d), 64.5 (t), 63.9 (d), 59.4 (d), 58.3 (t), 57.4 (d), 56.9 (d), 54.3 (d), 48.7 (t), 41.5 (t), 41.5 (t), 39.9 (t), 35.5 (t), 31.5 (t), 29.1 (t)

From the analysis of the above physical and chemical properties, and the result of the further investigation of identification of chemical structure, the chemical structure of the Deacyl WF 738F has been identified and assigned as follows.

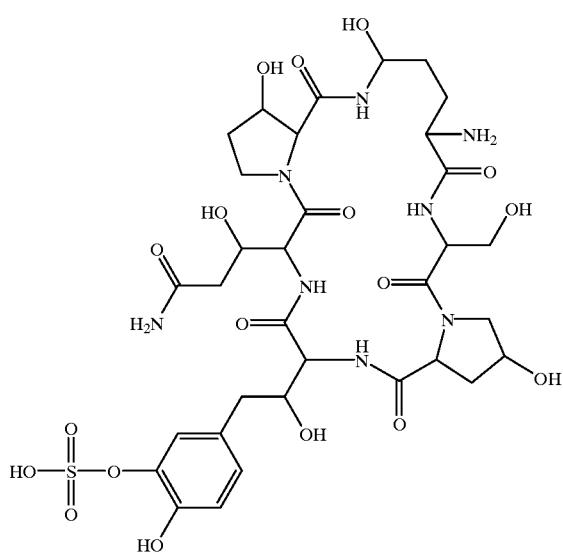

What is claimed is:

1. A polypeptide compound of the following general formula (I):

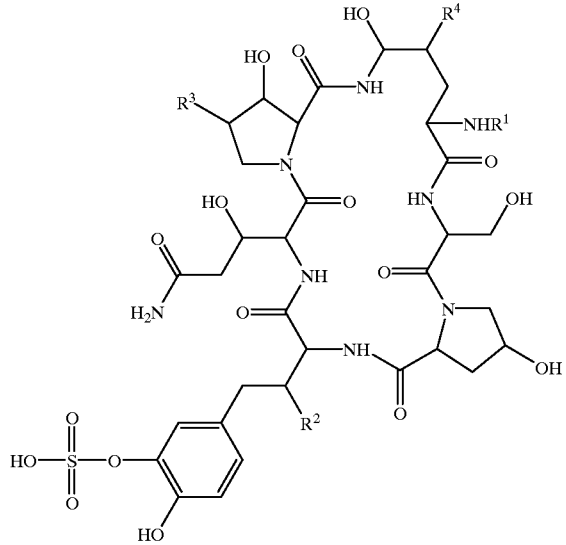

(I)

wherein

R$^1$ is hydrogen or acyl group,

R$^2$ is hydrogen or hydroxy,

R$^3$ is hydrogen or methyl, and

R$^4$ is hydrogen or hydroxy, with proviso that when R$^4$ is hydroxy, then R$^2$ is hydroxy, or a salt thereof.

2. A compound of claim 1, wherein R$^1$ is hydrogen, aroyl having higher alkoxy, aroyl substituted with heterocyclic group which has aryl having lower alkoxy, aroyl substituted with heterocyclic group which has aryl having higher alkoxy, ar(lower)alkenoyl substituted with aryl having lower alkoxy, ar(lower)alkenoyl substituted with aryl having higher alkoxy, aroyl substituted with aryl which has aryl having lower alkoxy, aroyl substituted with aryl which has aryl having higher alkoxy, aroyl substituted with heterocyclic group which has aryl substituted with aryl having lower alkoxy, or aroyl substituted with heterocyclic group which has aryl substituted with aryl having higher alkoxy.

3. A compound of claim 2, wherein R$^1$ is hydrogen.

4. A process for preparing a polypeptide compound of claim 1 or a salt thereof, which comprises i) fermenting a strain belonging to the genus Coleophoma which is capable of producing a compound of the formula (Ia) or a salt thereof:

(Ia)

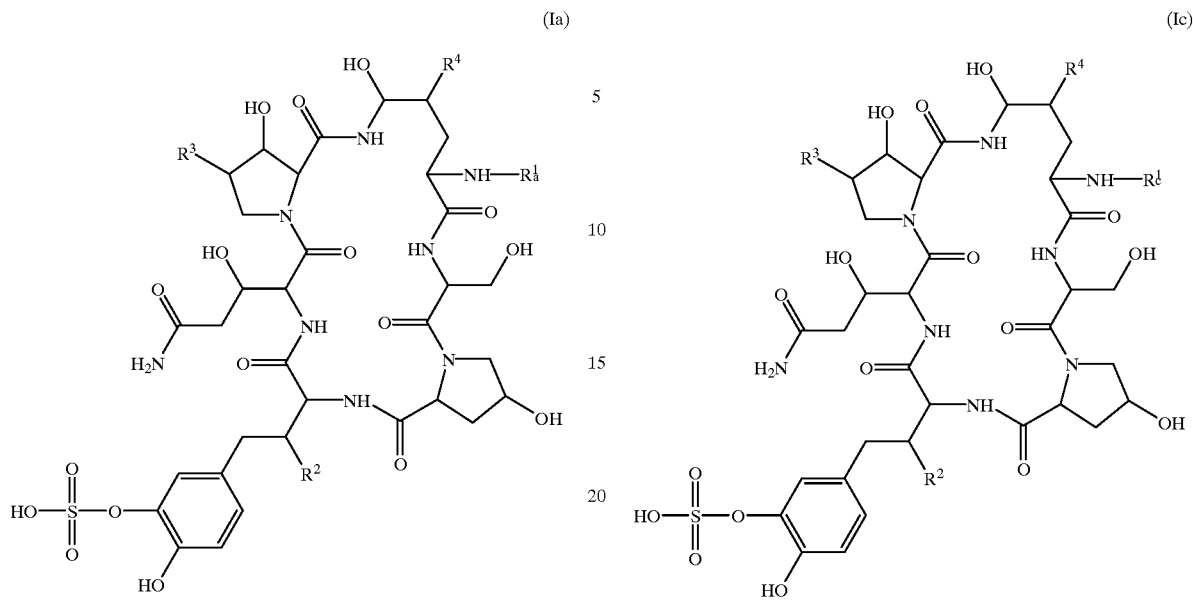

wherein $R_a^1$ is palmitoyl and
$R^2$, $R^3$ and $R^4$ are each as defined in claim 1, in a nutrient medium and recovering the compound (Ia) or a salt thereof, to give the compound (Ia) or a salt thereof;

ii) subjecting a compound of (Ia) or a salt thereof, to elimination reaction of N-acyl group, to give a compound of the formula (Ib):

(Ib)

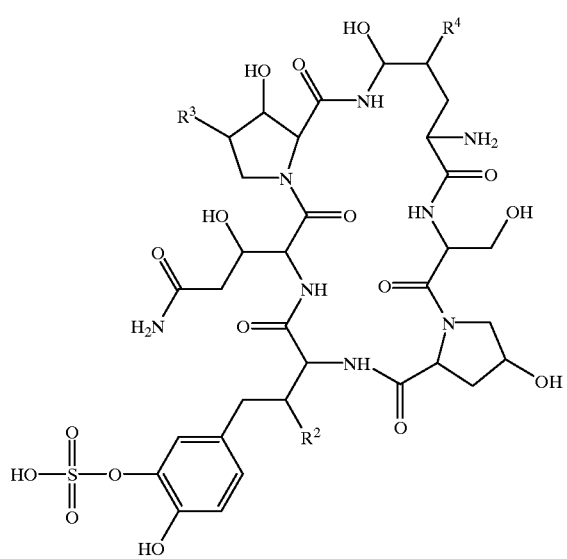

wherein $R^2$, $R^3$ and $R^4$ are each as defined in claim 1, or a salt thereof; or iii) subjecting a compound of (Ib) or a salt thereof thus obtained to acylation reaction, to give a compound of the formula (Ic):

(Ic)

wherein $R_c^1$ is acyl group exclusive of palmitoyl,
$R^2$, $R^3$ and $R^4$ are each as defined in claim 1, or a salt thereof.

5. A pharmaceutical composition or medicament comprising the compound of claim 1 or a pharmaceutically acceptable salt thereof in admixture with a pharmaceutically acceptable carrier, diluent or excipient.

6. An antimicrobial agent comprising the compound of claim 1, or a pharmaceutically acceptable salt thereof.

7. An antifungal agent comprising the compound of claim 1, or a pharmaceutically acceptable salt thereof.

8. A method for the prophylactic or the therapeutic treatment of an infectious disease caused by a pathogenic microorganism comprising administering the compound of claim 1, or a pharmaceutically acceptable salt thereof to a human being or an animal.

9. An isolated microorganism *Coleophoma crateriformis* No. 738 (FERM BP-5796).

10. A polypeptide compound or a pharmaceutically acceptable salt thereof which is obtained by culturing *Coleophoma crateriformis* No. 738 in a medium capable of supporting this strain.

11. The method of claim 8, wherein said disease is a fungal disease.

12. The method of claim 8, wherein said disease is caused by a microorganism selected from the group consisting of Aspergillus, Cyptococcus, Candida, Mucor, Actinomyces, Histoplasma, Dermatophyte, Malassezia, Fusarium and Pneumocystis.

13. The method of claim 8, wherein said disease is caused by *Pneumocystis carinii*.

14. The method of claim 8, wherein said compound is administered to a human.

15. The composition or medicament of claim 5, selected from the group consisting of a granule, tablet, dragee, pellet, troche, capsule, suppository, cream, ointment, aerosol, powder, aerosol spray, solution, emulsion, suspension, ingestion and eye drop.

* * * * *